United States Patent
Malik et al.

(10) Patent No.: US 11,959,856 B2
(45) Date of Patent: Apr. 16, 2024

(54) MULTIPLEXING AND QUANTIFICATION IN PCR WITH REDUCED HARDWARE AND REQUIREMENTS

(71) Applicant: CALIFORNIA INSTITUTE OF TECHNOLOGY, Pasadena, CA (US)

(72) Inventors: Imran R. Malik, Pasadena, CA (US); Xiomara Linnette Madero, Glendale, CA (US); Erika F. Garcia, Los Angeles, CA (US); Sheel Mukesh Shah, Los Angeles, CA (US); Axel Scherer, Barnard, VT (US)

(73) Assignee: California Institute of Technology, Pasadena, CA (US)

( * ) Notice: Subject to any disclaimer, the term of this patent is extended or adjusted under 35 U.S.C. 154(b) by 521 days.

(21) Appl. No.: 15/701,014

(22) Filed: Sep. 11, 2017

(65) Prior Publication Data

US 2018/0052110 A1 Feb. 22, 2018

Related U.S. Application Data

(62) Division of application No. 13/958,479, filed on Aug. 2, 2013, now Pat. No. 9,791,372.

(60) Provisional application No. 61/679,547, filed on Aug. 3, 2012.

(51) Int. Cl.
*G01N 21/64* (2006.01)
*C12Q 1/6851* (2018.01)

(52) U.S. Cl.
CPC ....... *G01N 21/6486* (2013.01); *C12Q 1/6851* (2013.01)

(58) Field of Classification Search
CPC .......................... G01N 21/6486; C12Q 1/6851
See application file for complete search history.

(56) References Cited

U.S. PATENT DOCUMENTS

| | | |
|---|---|---|
| 5,079,351 A | 1/1992 | Sninsky et al. |
| 5,538,848 A | 7/1996 | Livak et al. |
| 5,618,711 A | 4/1997 | Gelfand et al. |
| 5,677,152 A | 10/1997 | Birch et al. |
| 5,723,591 A | 3/1998 | Livak et al. |
| 5,773,258 A | 6/1998 | Birch et al. |
| 5,789,224 A | 8/1998 | Gelfand et al. |
| 5,804,375 A | 9/1998 | Gelfand et al. |
| 5,834,203 A * | 11/1998 | Katzir ............... G01N 21/6428 435/6.19 |
| 5,876,930 A | 3/1999 | Livak et al. |
| 5,882,856 A | 3/1999 | Shuber |
| 5,928,862 A | 7/1999 | Morrison |
| 5,948,360 A | 9/1999 | Rao et al. |
| 5,981,180 A | 11/1999 | Chandler et al. |
| 5,994,056 A | 11/1999 | Higuchi |
| 6,030,787 A | 2/2000 | Livak et al. |
| 6,103,463 A | 8/2000 | Chetverin et al. |
| 6,127,155 A | 10/2000 | Gelfand et al. |
| 6,171,785 B1 | 1/2001 | Higuchi |
| 6,258,569 B1 | 7/2001 | Livak et al. |
| 6,534,266 B1 | 3/2003 | Singer |
| 6,534,274 B2 | 3/2003 | Becker et al. |
| 6,548,259 B2 | 4/2003 | Ward et al. |
| 6,642,062 B2 | 11/2003 | Kauvar et al. |
| 6,893,875 B2 | 5/2005 | Tsuji et al. |
| 7,101,663 B2 | 9/2006 | Godfrey et al. |
| 7,141,377 B2 | 11/2006 | Gelfand et al. |
| 7,348,141 B2 | 3/2008 | French et al. |
| 7,385,043 B1 | 6/2008 | Kramer |
| 7,410,764 B2 | 8/2008 | Gocke et al. |
| 7,413,708 B2 | 8/2008 | Mayrand |
| 7,473,767 B2 | 1/2009 | Dimitrov |
| 7,507,575 B2 | 3/2009 | Bedingham et al. |
| 7,575,864 B2 | 8/2009 | Bedzyk et al. |
| 7,667,024 B2 | 2/2010 | Mao et al. |
| 7,671,184 B2 | 3/2010 | Haener et al. |
| 7,709,249 B2 * | 5/2010 | Bedingham ........... G01J 3/4406 435/288.7 |
| 7,767,423 B2 | 8/2010 | Kopreski et al. |
| 7,771,949 B2 | 8/2010 | Kramer |
| 7,919,237 B2 | 4/2011 | Dimitrov et al. |
| 7,919,244 B2 | 4/2011 | Madejon et al. |
| 7,930,106 B2 | 4/2011 | Carrick et al. |
| 7,941,279 B2 | 5/2011 | Hwang et al. |
| 8,039,215 B2 | 10/2011 | Higuchi et al. |
| 8,148,512 B2 | 4/2012 | Dimitrov et al. |

(Continued)

FOREIGN PATENT DOCUMENTS

| | | |
|---|---|---|
| CN | 1936019 A | 3/2007 |
| CN | 101570782 A | 11/2009 |

(Continued)

OTHER PUBLICATIONS

Arya et al., Basic principles of real-time quantitative PCR, 2005, Expert Rev. Mol. Diagn., 5(2), p. 209-219 (Year: 2005).*
Logan et al., An Overview of Real-Time PCR Platforms, 2004, In Real-time PCR: An Essential Guide, p. 13-30 (Year: 2004).*
Elnifro et al., Multiplex PCR: Optimization and Application in Diagnostic Virology, 2000, Clinical Microbiology Reviews, p. 559-570 (Year: 2000).*
Wittwer et al., Real-Time Multiplex PCR Assays, 2001, Methods, 25, p. 430-442 (Year: 2001).*
Markoulatos et al., Multiplex Polymerase Chain Reaction: A Practical Approach, 2002, 16, p. 47-51 (Year: 2002).*

(Continued)

*Primary Examiner* — Kaitlyn L Minchella
(74) *Attorney, Agent, or Firm* — Sheppard Mullin Richter & Hampton LLP

(57) ABSTRACT

Methods and algorithms for a multiplexed single detection channel amplification process and quantification of generated amplicons is presented. Various mathematical approaches for quantifying and verifying the amplicons in a reaction are presented. Usage of such methods and approaches allow upgrading of existing single and multiple channel instruments for further multiplexing capabilities.

7 Claims, 12 Drawing Sheets

(56) References Cited

U.S. PATENT DOCUMENTS

| | | |
|---|---|---|
| 8,426,132 B2 | 4/2013 | Li et al. |
| 8,455,184 B2 | 6/2013 | Atchley et al. |
| 8,492,094 B2 | 7/2013 | Dimitrov et al. |
| 8,519,115 B2 | 8/2013 | Webster et al. |
| 8,614,061 B2 | 12/2013 | Brabetz et al. |
| 8,771,955 B2 | 7/2014 | Reed et al. |
| 8,838,394 B2 | 9/2014 | Kartalov et al. |
| 8,877,464 B2 | 11/2014 | Babiel et al. |
| 8,962,250 B2 | 2/2015 | Stanley et al. |
| 9,133,506 B2 | 9/2015 | Katzir et al. |
| 9,222,128 B2 | 12/2015 | Saxonov et al. |
| 9,260,761 B2 | 2/2016 | Tyagi et al. |
| 9,366,632 B2 | 6/2016 | Link et al. |
| 9,422,593 B2 | 8/2016 | Rothmann et al. |
| 9,441,266 B2 | 9/2016 | Larson et al. |
| 9,447,457 B2 | 9/2016 | Chun et al. |
| 9,458,497 B2 | 10/2016 | Hassibi et al. |
| 9,791,372 B2 | 10/2017 | Malik et al. |
| 10,066,263 B2 | 9/2018 | Rajagopal et al. |
| 10,068,051 B2 | 9/2018 | Kartalov et al. |
| 2002/0022273 A1 | 2/2002 | Empedocles et al. |
| 2002/0146734 A1 | 10/2002 | Ortyn et al. |
| 2003/0134320 A1 | 7/2003 | Barrus et al. |
| 2003/0148280 A1 | 8/2003 | Harris et al. |
| 2003/0148544 A1 | 8/2003 | Nie et al. |
| 2004/0053230 A1 | 3/2004 | Schaffer et al. |
| 2004/0191794 A1 | 9/2004 | Weindel et al. |
| 2005/0053950 A1* | 3/2005 | Zudaire Ubani .... C12Q 1/6851 435/6.11 |
| 2005/0064435 A1 | 3/2005 | Su et al. |
| 2005/0106607 A1 | 5/2005 | Yin et al. |
| 2005/0164264 A1 | 7/2005 | Shipwash |
| 2005/0214753 A1 | 9/2005 | Shultz et al. |
| 2005/0250146 A1 | 11/2005 | McMillan |
| 2005/0260640 A1 | 11/2005 | Andersen et al. |
| 2006/0216708 A1 | 9/2006 | Venema |
| 2007/0072211 A1 | 3/2007 | Newton et al. |
| 2007/0178485 A1 | 8/2007 | El-Deiry et al. |
| 2007/0231824 A1 | 10/2007 | Chee et al. |
| 2008/0050737 A1 | 2/2008 | Arieli et al. |
| 2008/0069733 A1 | 3/2008 | Maltezos et al. |
| 2008/0096767 A1 | 4/2008 | Kohn |
| 2008/0124705 A1 | 5/2008 | Kramer et al. |
| 2009/0042735 A1 | 2/2009 | Blair et al. |
| 2009/0048785 A1 | 2/2009 | Katzir et al. |
| 2009/0062129 A1 | 3/2009 | McKernan et al. |
| 2010/0015607 A1 | 1/2010 | Geiss et al. |
| 2010/0047924 A1 | 2/2010 | Webster et al. |
| 2010/0112710 A1 | 5/2010 | Geiss et al. |
| 2010/0120043 A1 | 5/2010 | Sood et al. |
| 2010/0151443 A1 | 6/2010 | Xiang et al. |
| 2010/0159447 A1 | 6/2010 | Li et al. |
| 2010/0210472 A1 | 8/2010 | Empedocles et al. |
| 2010/0233686 A1 | 9/2010 | Higuchi et al. |
| 2010/0248257 A1 | 9/2010 | Jacobsen et al. |
| 2010/0261026 A1 | 10/2010 | Ferree et al. |
| 2010/0267064 A1 | 10/2010 | Kartalov et al. |
| 2010/0273173 A1 | 10/2010 | Hirai et al. |
| 2010/0324834 A1 | 12/2010 | Treptow et al. |
| 2011/0104684 A1 | 5/2011 | Hooper |
| 2011/0151459 A1 | 6/2011 | Rothmann et al. |
| 2011/0151550 A1 | 6/2011 | Sagner et al. |
| 2011/0171658 A1 | 7/2011 | Carrick |
| 2011/0207623 A1 | 8/2011 | Dimitrov et al. |
| 2011/0223602 A1 | 9/2011 | Whitman et al. |
| 2011/0237459 A1 | 9/2011 | Nova et al. |
| 2012/0003646 A1 | 1/2012 | Joo et al. |
| 2012/0040349 A1 | 2/2012 | Von et al. |
| 2012/0040352 A1 | 2/2012 | Wangh et al. |
| 2012/0045756 A1 | 2/2012 | Rothmann et al. |
| 2012/0077195 A1 | 3/2012 | Li et al. |
| 2012/0101740 A1 | 4/2012 | Orpana et al. |
| 2012/0122704 A1 | 5/2012 | Atchley et al. |
| 2012/0141995 A1 | 6/2012 | Li et al. |
| 2012/0171677 A1 | 7/2012 | Ludowise |
| 2012/0184017 A1 | 7/2012 | Chatterjee |
| 2012/0190030 A1 | 7/2012 | Chun et al. |
| 2012/0196283 A1 | 8/2012 | Babiel et al. |
| 2012/0244534 A1 | 9/2012 | Ching et al. |
| 2012/0252014 A1 | 10/2012 | Loeffert et al. |
| 2012/0252017 A1 | 10/2012 | Reed et al. |
| 2012/0258457 A1 | 10/2012 | Jarosch et al. |
| 2012/0302448 A1 | 11/2012 | Hutchison et al. |
| 2013/0017971 A1 | 1/2013 | Geiss et al. |
| 2013/0040841 A1 | 2/2013 | Saxonov et al. |
| 2013/0078626 A1 | 3/2013 | Wasserstrom et al. |
| 2013/0116780 A1 | 5/2013 | Miller et al. |
| 2013/0261019 A1 | 10/2013 | Lin et al. |
| 2013/0288244 A1 | 10/2013 | Deciu et al. |
| 2014/0004520 A1 | 1/2014 | Mohapatra et al. |
| 2014/0038195 A1 | 2/2014 | Malik et al. |
| 2014/0171341 A1 | 6/2014 | Jouvenot et al. |
| 2014/0213471 A1 | 7/2014 | Rajagopal et al. |
| 2014/0274774 A1 | 9/2014 | Li et al. |
| 2015/0057178 A1 | 2/2015 | Kartalov et al. |
| 2015/0140554 A1 | 5/2015 | Snyder et al. |
| 2015/0211054 A1 | 7/2015 | Kostem et al. |
| 2015/0275295 A1 | 10/2015 | Wang et al. |
| 2016/0040256 A1 | 2/2016 | Chen et al. |
| 2016/0108464 A1 | 4/2016 | Saxonov et al. |
| 2016/0201122 A1 | 7/2016 | Bushkin et al. |
| 2016/0273048 A1 | 9/2016 | Roperch |
| 2017/0145490 A1 | 5/2017 | Chiu et al. |
| 2017/0314073 A1 | 11/2017 | Grömminger et al. |
| 2017/0362636 A1 | 12/2017 | Rajagopal et al. |
| 2018/0030551 A1 | 2/2018 | Rajagopal et al. |
| 2018/0057864 A1 | 3/2018 | Jacky et al. |
| 2019/0112636 A1 | 4/2019 | Rajagopal et al. |
| 2019/0233882 A1 | 8/2019 | Jacky et al. |

FOREIGN PATENT DOCUMENTS

| | | |
|---|---|---|
| CN | 101831496 A | 9/2010 |
| CN | 102269759 A | 12/2011 |
| CN | 102439171 A | 5/2012 |
| CN | 102559868 A | 7/2012 |
| CN | 102576390 A | 7/2012 |
| CN | 104662172 B | 7/2018 |
| EP | 0519338 A1 | 12/1992 |
| EP | 1448581 B1 | 11/2008 |
| EP | 2224017 A1 | 9/2010 |
| EP | 1963531 B1 | 9/2011 |
| EP | 1629108 B1 | 12/2014 |
| WO | WO-9746714 A1 | 12/1997 |
| WO | WO-9919515 A1 | 4/1999 |
| WO | WO-9952708 A1 | 10/1999 |
| WO | WO-0107640 A2 | 2/2001 |
| WO | 01/59144 A1 | 8/2001 |
| WO | WO-02056014 A2 | 7/2002 |
| WO | WO-03002979 A2 | 1/2003 |
| WO | WO-03020967 A1 | 3/2003 |
| WO | WO-02056014 A3 | 10/2003 |
| WO | WO-2004087950 A2 | 10/2004 |
| WO | WO-2006079049 A2 | 7/2006 |
| WO | WO-2007076128 A2 | 7/2007 |
| WO | WO-2007076129 A2 | 7/2007 |
| WO | WO-2007076132 A2 | 7/2007 |
| WO | WO-2007076132 A3 | 9/2007 |
| WO | WO-2007076128 A3 | 11/2007 |
| WO | WO-2007139766 A2 | 12/2007 |
| WO | WO-2007076129 A3 | 3/2008 |
| WO | WO-2008118998 A2 | 10/2008 |
| WO | WO-2008124847 A2 | 10/2008 |
| WO | WO-2007139766 A3 | 12/2008 |
| WO | WO-2008124847 A3 | 2/2009 |
| WO | WO-2009036514 A2 | 3/2009 |
| WO | WO-2010007355 A1 | 1/2010 |
| WO | WO-2010013017 A1 | 2/2010 |
| WO | WO-2010017543 A1 | 2/2010 |
| WO | WO-2010019826 A1 | 2/2010 |
| WO | WO-2010128206 A1 | 11/2010 |
| WO | WO-2011047087 A2 | 4/2011 |
| WO | WO-2011047087 A3 | 8/2011 |
| WO | WO-2011100541 A2 | 8/2011 |

(56) References Cited

FOREIGN PATENT DOCUMENTS

| WO | WO-2011116088 A2 | 9/2011 |
| WO | WO-2011100541 A3 | 1/2012 |
| WO | WO-2011116088 A3 | 2/2012 |
| WO | 2012/056227 A1 | 5/2012 |
| WO | WO-2012058638 A2 | 5/2012 |
| WO | WO-2012106428 A2 | 8/2012 |
| WO | WO-2012135340 A2 | 10/2012 |
| WO | WO-2012058638 A3 | 12/2012 |
| WO | WO-2012135340 A3 | 12/2012 |
| WO | WO-2013096851 A1 | 6/2013 |
| WO | WO-2013116780 A1 | 8/2013 |
| WO | WO-2014022827 A1 | 2/2014 |
| WO | WO-2014116884 A1 | 7/2014 |
| WO | WO-2015147370 A1 | 10/2015 |
| WO | WO-2017139354 A1 | 8/2017 |
| WO | WO-2017173035 A1 | 10/2017 |
| WO | WO-2017218777 A1 | 12/2017 |
| WO | WO-2018081178 A1 | 5/2018 |
| WO | WO-2019006023 A1 | 1/2019 |
| WO | WO-2019079204 A1 | 4/2019 |
| WO | WO-2019169043 A1 | 9/2019 |

OTHER PUBLICATIONS

Sanchez et al., Linear-After-The-Exponential (LATE)-PCR: An advanced method of asymmetric PCR and its uses in quantitative real-time analysis, 2004, 101(7), p. 1933-1938 (Year: 2004).*

Belak et al., Novel and Rapid Technologies for the Early Diagnosis and Molecular Epidemiology of Viral Diseases, 2010, Sustainable Improvement of Animal Production and Health, Food and Agriculture Organization of the United Nations, Rome, p. 295-303 (Year: 2010).*

Beige, et al. Clinical evaluation of a Mycobacterium tuberculosis PCR assay. J Clin Microbiol. Jan. 1995;33(1):90-5.

Blacket et al. Universal primers for fluorescent labeling of PCR fragments—an efficient and cost-effective approach to genotyping by fluorescence. Moleular Ecology Resources 12(3):456-463 (2012) Epub Jan. 24, 2012.

Chamberlain, et al. Deletion screening of the Duchenne muscular dystrophy locus via multiplex DNA amplification. Nucleic Acids Res. Dec. 9, 1988;16(23):11141-56.

Chapin et al., Rapid microRNA profiling on encoded gel microparticles. Angewandte Chemie International Edition, 50(10):2289-2293, 2011.

Chen, et al. A Homogeneous, ligase-mediated DNA diagnostic test. Genome Research, 1998, vol. 8, pp. 549-556.

Chong, et al. Single-tube multiplex-PCR screen for common deletional determinants of alpha-thalassemia. Blood. Jan. 1, 2000;95(1):360-2.

Chromatogram, 2011, 2 pages. Dorland's illustrated medical dictionary. Retrieved online on Jan. 22, 2014 from «http://www.credoreference.com».

Chun et al. Dual priming oligonucleotide system for the multiplex detection of respiratory viruses and SNP genotyping of CYP2C19 gene. Nucleic Acids Res. 35(6):e40 (2007).

Co-pending U.S. Appl. No. 15/914,356, filed Mar. 7, 2018.
Co-pending U.S. Appl. No. 16/020,673, filed Jun. 27, 2018.
Co-pending U.S. Appl. No. 16/051,736, filed Aug. 1, 2018.
Co-pending U.S. Appl. No. 16/128,343, filed Sep. 11, 2018.

Craig, et al. Ordering of cosmid clones covering Herpes simplex virus type I (HSV-I) genome: a test case for fingerprinting by hybridisation. Nucleic Acids Research, 1990, vol. 18, pp. 2653-2660.

Dos Santos, et al. A simple one-step real-time RT-PCR for diagnosis of dengue virus infection. J Med Virol. Aug. 2008;80(8):1426-33.

El-Hajj, et al. Detection of rifampin resistance in Mycobacterium tuberculosis in a single tube with molecular beacons. J Clin Microbiol. Nov. 2001;39(11):4131-7.

EMBL-Bank: AJ303204. http://www.ebi.ac.uk/Tools/dbfetch/emblfetch?db=embl&id=AJ303204&format=default&style=default&Retrieve=Retrieve. Accessed Feb. 2012.

EMBL-Bank: GQ395623. http://www.ebi.ac.uk/Tools/dbfetch/emblfetch?db=embl&id=GQ395623&format=default&style=default&Retrieve=Retrieve. Accessed Feb. 2012.

European Office Action for Patent Application No. EP13824744.0 dated Nov. 6, 2018.

Evans et al. Digital PCR for Noninvasive Detection of Aneuploidy: Power Analysis Equations for Feasibility. Fetal Diagn. Ther. 31:244-247(2012).

Extended European Search Report for Patent Application No. 13744261.2 dated May 3, 2016.

Extended European Search Report for Patent Application No. EP13824744.0 dated Feb. 26, 2016.

First Office Action for Chinese Patent Application No. 201380049844.9 dated Dec. 28, 2015 (w/translation).

Fodor, et al. Multiplexed biochemical assays with biological chips. Nature. Aug. 5, 1993;364(6437):555-6.

Fortina, et al. Digital mRNA profiling. Nat Biotechnol. Mar. 2008;26(3):293-4.

Fu et al. Multiplex detection and SNP genotyping in a single fluorescence channel. PLoS One 7(1):Article No. e30340 (Jan. 2012).

Gandelman, et al., Novel Bioluminescent Quantitative Detection of Nucleic Acid Amplification in Real-Time, PLoS One, 2010, 5(11):e14155, 14 pages.

GenBank: M93130.1. Dengue type 3 virus complete genome RNA, complete cds. http://www.ncbi.nlm.nih.gov/nuccore/M93130. Accessed Feb. 2012.

Han et al., Quantum-dot-tagged microbeads for multiplexed optical coding of biomolecules. Nature Biotechnology, 19(7):631-635, 2001.

Hartman, et al. Development of a novel internal positive control for Taqman based assays. Mol Cell Probes. Feb. 2005;19(1):51-9. Epub Dec. 10, 2004.

Haustein et al. Fluorescence correlation spectroscopy: novel variations of an established technique. Ann Rev Biophys Biomol Struct 36:151-69 (2007).

Heidari, et al. Detection of Plasmodium falciparum Directly from Blood Samples Using the Polymerase Chain Reaction. Journal of Sciences, Islamic Republic of Iran. 2005 16(1):21-24.

Henegariu, et al. Multiplex PCR: critical parameters and step-by-step protocol. Biotechniques. Sep. 1997;23(3):504-11.

HIV databases. http://www.hiv.lanl.gov/content/index. Accessed Feb. 2012.

Holland, et al., Detection of specific polymerase chain reaction product by utilizing the 5' to 3' exonuclease activity of Thermus aquaticus DNA polymerase. PNAS (USA) 88:7276-7280, 1991.

Horejsh, et al. A molecular beacon, bead-based assay for the detection of nucleic acids by flow cytometry. Nucleic Acids Res. Jan. 19, 2005;33(2):e13.

Huang, et al. Identification of 8 foodborne pathogens by multicolor combinational probe coding technology in a single real-time PCR. Clin Chem. Oct. 2007;53(10):1741-8. Epub Aug. 10, 2007.

Huang, et al. Multicolor combinatorial probe coding for real-time PCR. PLoS One. Jan. 14, 2011;6(1):e16033.

Hudecova, I. et al. Maternal Plasma Fetal DNA Fractions in Pregnancies with Low and High Risks for Fetal Chromosomal Aneuploidies. PLoS One 9(2):e88484 (2014) . . . .

Jothikumar, et al. Design of FRET-TaqMan probes for multiplex real-time PCR using an internal positive control. Biotechniques. Jun. 2009;46(7):519-24.

Klostranec et al., Convergence of quantum dot barcodes with microfluidics and signal processing for multiplexed high-throughout infectious disease diagnostics. Nano Letters, 7(9):2812-2818, 2007.

Kuhn, et al. Hybridization of DNA and PNA molecular beacons to single-stranded and double-stranded DNA targets. J Am Chem Soc. Feb. 13, 2002;124(6):1097-103.

Lao, et al. Multiplexing RT-PCR for the detection of multiple miRNA species in small samples. Biochem Biophys Res Commun. Apr. 28, 2006;343(1):85-9. Epub Feb. 28, 2006.

Lee, et al. Novel multiplex PCR using dual-priming oligonucleotides for detection and discrimination of the Mycobacterium tuberculosis complex and M. bovis BCG. J Clin Microbiol. Dec. 2010;48(12):4612-4. Epub Oct. 13, 2010.

(56) References Cited

OTHER PUBLICATIONS

Lee, et al. Seven-color, homogeneous detection of six PCR products. Biotechniques. Aug. 1999;27(2):342-9.
Li et al., Multiplexed detection of pathogen DNA with DNA-based fluorescence nanobarcodes. Nature Biotechnology, 23(7):885-889, 2005.
Liew, et al. Validating a custom multiplex ELISA against individual commercial immunoassays using clinical samples. Biotechniques. Mar. 2007;42(3):327-8, 330-3.
Lin et al., Self-assembled combinatorial encoding nanoarrays for multiplexed biosensing. Nano Letters, 7(2):507-512, 2007.
Livak, et al. Oligonucleotides with fluorescent dyes at opposite ends provide a quenched probe system useful for detecting PCR product and nucleic acid hybridization. PCR Methods Appl. Jun. 1995;4(6):357-62.
Morrison, et al. Two-color ratio-coding of chromosome targets in fluorescence in situ hybridization: quantitative analysis and reproducibility. Cytometry. Apr. 1, 1997;27(4):314-26.
Noordhoek, et al. Sensitivity and specificity of PCR for detection of *Mycobacterium tuberculosis*: a blind comparison study among seven laboratories. J Clin Microbiol. Feb. 1994;32(2):277-84.
Oliveira, et al. Multiplex PCR strategy for rapid identification of structural types and variants of the mec element in methicillin-resistant *Staphylococcus aureus*. Antimicrob Agents Chemother. Jul. 2002;46(7):2155-61.
Ou, et al. DNA amplification for direct detection of HIV-1 in DNA of peripheral blood mononuclear cells. Science. Jan. 15, 1988;239(4837):295-7.
Paton, et al. Detection and characterization of Shiga toxigenic *Escherichia coli* by using multiplex PCR assays for stx1, stx2, eaeA, enterohemorrhagic *E. coli* hlyA, rfbO111, and rfbO157. J Clin Microbiol. Feb. 1998;36(2):598-602.
Patterson, et al. Detection of HIV-1 DNA and messenger RNA in individual cells by PCR-driven in situ hybridization and flow cytometry. Science. May 14, 1993;260(5110):976-9.
PCT/US2013/024509 International search report and written opinion dated Apr. 12, 2013.
PCT/US2013/053512 International Search Report and Written Opinion dated Oct. 16, 2013.
PCT/US2017/24933 International search report and written report dated Jun. 22, 2017.
PCT/US2017/37682 International Search Report and Written Opinion dated Nov. 16, 2017.
PCT/US2018/39846 International Search Report and Written Opinion dated Sep. 14, 2018.
Petersen, et al. Short PNA molecular beacons for real-time PCR allelic discrimination of single nucleotide polymorphisms. Mol Cell Probes. Apr. 2004;18(2):117-22.
Plasmodium falciparum (Plasmodium falciparum) Genome Browser Gateway. http://microbes.ucsc.edu/cgi-bin/hgGateway?hgsid=612764&clade=eukaryota-protista&org=0&db=0. Accessed Feb. 2012.
Ptak, et al. Inhibition of human immunodeficiency virus type 1 replication in human cells by Debio-025, a novel cyclophilin binding agent. Antimicrob Agents Chemother. Apr. 2008;52(4):1302-17. Epub Jan. 22, 2008.
Rajagopal et al. Supercolor Coding Methods for Large-Scale Multiplexing of Biochemical Assays. Analytical Chemistry 85:7629-7636 (2013).
Rosenstraus, et al. An internal control for routine diagnostic PCR: design, properties, and effect on clinical performance. J Clin Microbiol. Jan. 1998;36(1):191-7.
Roth, et al. Feasibility and efficacy of routine PCR screening of blood donations for hepatitis C virus, hepatitis B virus, and HIV-1 in a blood-bank setting. Lancet. Jan. 30, 1999;353(9150):359-63.
Saiki, et al. Primer-directed enzymatic amplification of DNA with a thermostable DNA polymerase. Science, 239(4839):487-491 (Jan. 29, 1988).
Sanger, et al. DNA sequencing with chain-terminating inhibitors. Proc Natl Acad Sci U S A. Dec. 1977;74(12):5463-7.
Second Office Action for Chinese Patent Application No. 201380049844.9 dated Sep. 19, 2016 (w/translation).
Speicher, et al. Karyotyping human chromosomes by combinatorial multi-fluor FISH. Nat Genet. Apr. 1996;12(4):368-75.
ThermoFisher Scientific Fluorescence SpectraViewer. Retrieved from http://www.thermofisher.com/us/en/home/life-science/cell-analysis/labeling-chemistry/fluorescence-spectraviewer.html on Sep. 25, 2015.
Tirasophon, et al. A novel detection of a single Plasmodium falciparum in infected blood. Biochem Biophys Res Commun. Feb. 28, 1991;175(1):179-84.
Tyagi, et al. Multicolor molecular beacons for allele discrimination. Nat Biotechnol. Jan. 1998;16(1):49-53.
Tyagi, et al. Wavelength-shifting molecular beacons. Nat Biotechnol. Nov. 2000;18(11):1191-6.
Urdea, et al. Requirements for high impact diagnostics in the developing world. Nature. Nov. 23, 2006;444 Suppl 1:73-9.
U.S. Appl. No. 13/756,760 Notice of allowance dated Jun. 2, 2014.
U.S. Appl. No. 13/756,760 Office action dated Jan. 24, 2014.
U.S. Appl. No. 13/958,479 Office Action dated Mar. 1, 2016.
U.S. Appl. No. 14/451,876 Office action dated Jun. 6, 2017.
U.S. Appl. No. 14/451,876 Office action dated Nov. 23, 2016.
U.S. Appl. No. 15/623,974 Notice of Allowance dated Jul. 3, 2018.
U.S. Appl. No. 15/623,974 Office Action dated Feb. 22, 2018.
U.S. Appl. No. 15/677,772 Final Office Action dated Jun. 7, 2018.
U.S. Appl. No. 15/677,772 Office Action dated Feb. 8, 2018.
U.S. Appl. No. 15/892,245 First Action Interview—Office Action dated Jul. 19, 2018.
U.S. Appl. No. 15/892,245 Preinterview First Interview Office Action dated May 11, 2018.
U.S. Appl. No. 14/451,876 Notice of Allowance dated Jul. 11, 2018.
U.S. Appl. No. 14/451,876 Notice of Allowance dated Jun. 14, 2018.
Vet, et al. Multiplex detection of four pathogenic retroviruses using molecular beacons. Proc Natl Acad Sci U S A. May 25, 1999;96(11):6394-9.
Wang, et al. Locked nucleic acid molecular beacons. J Am Chem Soc. Nov. 16, 2005;127(45):15664-5.
Waters, et al. Microchip device for cell lysis, multiplex PCR amplification, and electrophoretic sizing. Anal Chem. Jan. 1, 1998;70(1):158-62.
Weidmann, et al. Rapid detection of herpes simplex virus and varicella-zoster virus infections by real-time PCR. J Clin Microbiol. Apr. 2003;41(4):1565-8.
Wiese, et al. Simultaneous multianalyte ELISA performed on a microarray platform. Clin Chem. Aug. 2001;47(8):1451-7.
Xu et al., Multiplexed SNP genotyping using the Qbead system: a quantum dot-encoded microspere-based assay. Nucleic Acids Research, 31(8):e43, 2003.
Yang, L. et al. A novel universal real-time PCR system using the attached universal duplex probes for quantitative analysis of nucleic acids. BMC Molecular Biology, 9:54 (1-13) Jun. 4, 2008.
Zhang, et al. A novel real-time quantitative PCR method using attached universal template probe. Nucleic Acids Res. Oct. 15, 2003;31(20):e123(pp. 1-8).
Zhang, et al. Novel Multiplex PCR Assay for Characterization and Concomitant Subtyping of Staphylococcal Cassette Chromosome mec Types I to V in Methicillin-Resistant *Staphylococcus aureus*. J Clin Microbiol. Oct. 2005;43(10):5026-33.
Zhao et al. Comprehensive Algorithm for Quantitative Real-Time Polymerase Chain Reaction. Journal of Computational Biology 12(8):1047-1064 (2005).
Co-pending U.S. Appl. No. 16/537,415, filed Aug. 9, 2019.
Co-pending U.S. Appl. No. 16/864,744, filed May 1, 2020.
EP17814096.8 Extended European Search Report dated Dec. 2, 2019.
EP18181686.9 Extended European Search Report dated Jul. 23, 2019.
PCT/US2018/039846 International Preliminary Report on Patentability dated Dec. 31, 2019.
U.S. Appl. No. 16/128,343 Office Action dated Oct. 15, 2019.
U.S. Appl. No. 15/914,356 Office Action dated Jul. 22, 2019.
U.S. Appl. No. 15/914,356 Office Action dated Mar. 8, 2019.

(56) References Cited

OTHER PUBLICATIONS

U.S. Appl. No. 16/128,343 First Action Interview dated Apr. 18, 2019.
Vogelstein, et al., Digital PCR, PNAS Aug. 3, 1999 96 (16) 9236-9241; https://doi.org/10.1073/pnas.96.16.9236.
European Patent Application No. 17776626 Office Action dated Oct. 18, 2019.
International Search Report and Written Opinion dated Nov. 21, 2019 for PCT/US2019/050050.
Loftis et al., Principles of real-time PCR. Veterinary PCR Diagnostics pp. 3-17 (2012).
Morgan et al., A commercial line probe assay for the rapid detection of rifampicin resistance in *Mycobacterium tuberculosis*: a systematic review and meta-analysis. BMC Infectious Diseases. 5:62 doi:10.1186/1471-2334-5-62 (2005).
Navarro et al., Real-time PCR detection chemistry. Clin Chim Acta. 439:231-250 (2015).
PCT/US19/40392 International Search Report and Written Opinion dated Nov. 6, 2019.
PCT/US2018/055927 International Preliminary Report on Patentability dated Apr. 21, 2020.
PCT/US2019/019906 International Preliminary Report on Patentability Sep. 1, 2020.
PCT/US2019/019906 International Search Report and Written Opinion dated May 6, 2019.
PCT/US2019/027751 International Preliminary Report on Patentability dated Oct. 20, 2020.
PCT/US2019/027751 International Search Report and Written Opinion dated Jun. 26, 2019.
PCT/US2019/035129 Invitation to Pay Additional Fees dated Aug. 19, 2019.
PCT/US2019/041239 International Search Report and Written Opinion dated Sep. 30, 2019.
Pierce, et al. Linear-After-The-Exponential (LATE)-PCR: primer design criteria for high yields of specific single-stranded DNA and improved real-time detection. Proc Natl Acad Sci U S A. Jun. 14, 2005; 102(24):8609-14. Epub Jun. 3, 2005.
Rajagopal et al., Significant Expansion of Real-Time PCR Multiplexing with Traditional Chemistries using Amplitude Modulation. Scientific Reports. 9(1): 1053 (2019) . . . .
Rickert et al., "Multiplexed Real-Time PCR Using Universal Reporters," Clin. Chem., 50(9): 1680-1683, 2004.
U.S. Appl. No. 15/892,245 Office Action dated Dec. 31, 2018.
U.S. Appl. No. 16/020,673 Non-Final Office Action dated Nov. 27, 2020.
U.S. Appl. No. 15/892,245 Office Action dated Dec. 11, 2019.
U.S. Appl. No. 15/892,245 Office Action dated Jun. 17, 2019.
U.S. Appl. No. 16/128,343 Non-Final Office Action dated Jun. 16, 2020.
U.S. Appl. No. 16/051,736 Office Action dated Aug. 21, 2020.
Extended European Search Report in EP Patent Application No. 21165520.4, dated Sep. 24, 2021.
Fu, Guoliang et al., "Multiplex Detection and SNP Genotyping in a Single Fluorescence Channel," PLOS One, Public Library of Science, US, vol. 7, No. 1, Jan. 1, 2012, pp. e30340-e30341.
First Search dated Mar. 26, 2021, issued in related Chinese Application No. 201810614480.9 (3 pages).

* cited by examiner

Amplitude normalized:
These two amplification curves with same Ct should overlap for minimum cumulative point wise distance.

Amplitude not normalized:
These two amplification curves with same Ct are not at correct location for minimum cumulative point wise distance.

MULTIPLEXING AND QUANTIFICATION IN PCR WITH REDUCED HARDWARE AND REQUIREMENTS

CROSS REFERENCE TO RELATED APPLICATIONS

This application is a divisional application of U.S. patent application Ser. No. 13/958,479 filed on Aug. 2, 2013, which, in turn, claims priority to Provisional Application 61/679,547 filed on Aug. 3, 2012, all of which are herein incorporated by reference in their entirety.

TECHNICAL FIELD

The present disclosure relates to the field of biochemical technology, and more specifically to methods and algorithms used in a multiplexed real-time quantitative polymerase chain reaction (qPCR) technology.

BACKGROUND

Multiplexing in real-time quantitative polymerase chain reaction (qPCR) allows detection and quantification of different amplified targets (e.g. amplicons) within a single qPCR assay, thus conserving sample material (e.g. enzyme, nucleotides, etc.) and avoiding well to well variation which can occur if multiplexing is done by splitting the sample into multiple separate chambers, well or tubes. Typical implementation of multiplexed qPCR requires reporters with different spectra (e.g. emission wavelengths) for each different amplicon and different detection channels to detect each of the different spectra. In one particular case, special reporters (e.g. target specific probes) are used to allow multiplexed qPCR using a same emission spectrum (e.g. wavelength) thus reducing the hardware required for the detection of the emission (e.g. reduced number of detection channels). Teachings according to the present disclosure allow for multiplexed qPCR and quantification in a single channel detection, by using, for example, simple non-specific dyes (e.g. intercalating dyes) and a same emission spectrum, thus providing a simple and cost effective multiplexing and quantification solution.

SUMMARY

According to a first aspect of the present disclosure, a method is provided, the method comprising: detecting a plurality of different amplicons generated during a multiplexed amplification reaction, using a single channel detector generating a sum amplitude signal in correspondence of the plurality of different amplicons; quantifying the plurality of detected different amplicons, and verifying the plurality of detected different amplicons, wherein the quantifying and the verifying comprise using mathematical analysis of the generated sum amplitude signal.

According to a second aspect of the present disclosure, a processor-based hardware analyzer for analyzing a multiplexed amplification reaction is provided, wherein the processor-based hardware analyzer is configured to quantify and verify the multiplexed amplification reaction based on a provided digital representation of a sum amplitude signal in correspondence of a plurality of different amplicons of the multiplexed amplification reaction.

BRIEF DESCRIPTION OF THE DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Figure 1A:
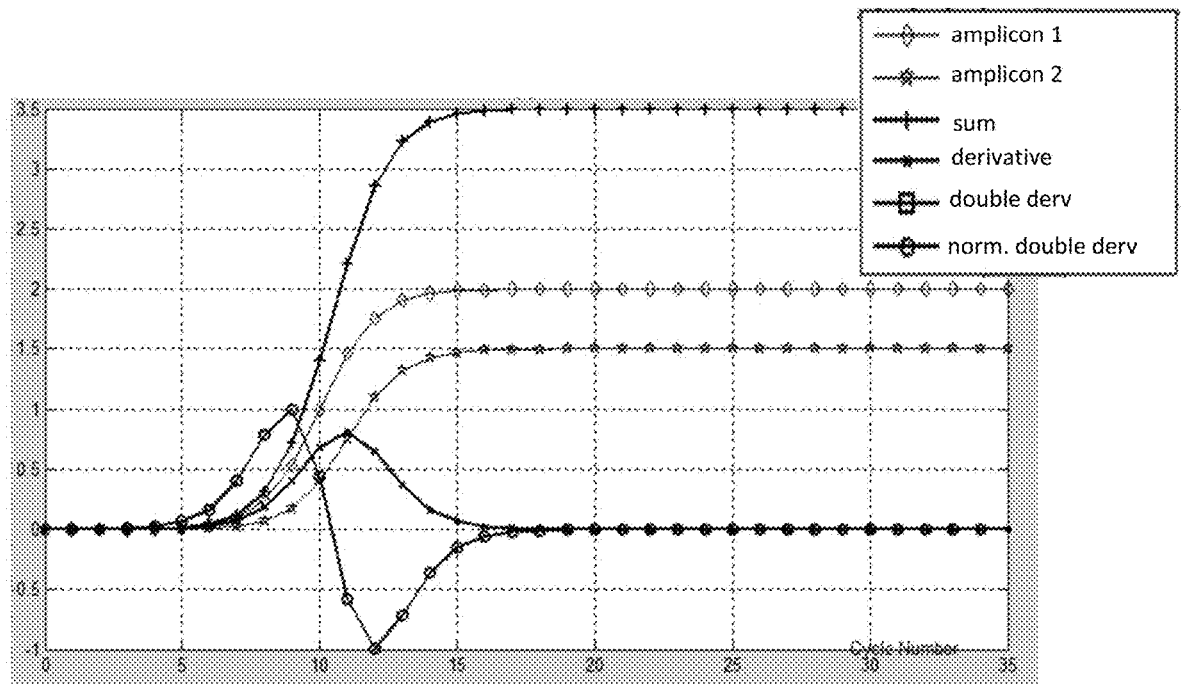
FIGS. 1A-1D show the various possible relationships between the amplitude curves of a multiplexed reaction with two amplicons.

According to several embodiments of the present disclosure, methods and algorithms for multiplexing and quantification of assays are disclosed. Such methods and algorithms can be used in conjunction with any technique which can measure total or targeted amplicon concentration during amplification, including but not limited to real-time quantitative polymerase chain reaction (qPCR) with fluorescence detection, electrochemical detection or any other real-time detection technique which can quantify the amount of DNA, whether total or specific.

For Point of Care (POC) applications, a single color multiplexing instrument (e.g. detecting single emission wavelength, single channel detection) has the benefits of being simpler, more compact and cheaper to manufacture as compared to a multi-color instrument. Such single color multiplexing instrument can also be faster since it can be more efficient in collecting emitted light and hence reducing the time needed to observe a corresponding signal. The skilled person will know that current multi-color instruments have the extra complexity of using dedicated detection channels per color, where each detection channel can contain a separate excitation light source, reflector, excitation filter, dedicated optical elements (e.g. prisms, gratings, dispersive elements, etc.) and narrow band (e.g. band pass)

emission filter, to detect a different emitted spectrum while rejecting other spectra used in the instrument. Due to overlapping emission spectra of dyes used in a multiplex real time qPCR, band pass filters are typically used to differentiate between the various emitted spectral bands, but a portion of the emission from the dye is not used to reduce spectral overlap, thus a less efficient detection can be obtained which can require a longer integration time.

According to some embodiments of the present disclosure, a single color (e.g. single detection channel) multiplexing instrument can be made by using absorbance, interference or combination of filters at the emission side with a wider bandwidth, such as a greater portion of an emission spectrum (e.g. wider range of wavelengths) can be used to detect the amplification process, which can in turn increase a detected signal intensity and thus reduce integration time while conducting fluorescence detection. According to further embodiments of the present disclosure, such single color multiplexing instrument can be used to detect, quantify and verify amplicons emitting at different wavelengths peaks associated to the different dyes and/or probes/primers used for each amplicon. In some cases, only portion of the emitted spectra associated to an amplicon is detected which can be taken into consideration during the quantification phase of the amplification process.

Testing for a disease is very useful in various applications. However, to ensure quality of a reaction, a positive and negative control is useful to determine whether contamination has occurred and whether the amplification is occurring properly. By conducting qPCR in one well (e.g. cartridge, reaction vessel), one can ease the design of fluidics, save reagents cost, as well as reduce error and contamination. Reducing of errors and contamination can in turn eliminate the requirement for addition of positive and negative controls in separate wells. In case of lyophilized reagents only the eluted DNA has to be added and the reaction can be run in one chamber.

Embodiments according to the present disclosure can be used in conjunction with various quantitative methods for detecting amplicon concentration using, for example, intercalating dyes which bind to any double string DNA in the assay, or methods using fluorophores attached to specific primers (e.g. Promega Plexor primers) which bind only to a targeted DNA string. Various other detection methods, using for example hybridization-probes such as hydrolysis, molecular beacons, fluorescence resonance energy transfer (FRET), hybridization, etc . . . , as well as electrochemical methods and electrophoresis methods are compatible with the various embodiments according to the present disclosure.

The various embodiments according to the present disclosure allow for multiplex detection and quantification of more targets (e.g. different targets) in the following cases (e.g. allows greater multiplexing)

a. Single fluorophore (e.g. single emission wavelength) for different targets using a single excitation (e.g. single wavelength). In such embodiments a same fluorophore, and thus a single detector, can be used with different sequence specific primers and yet detect different amplicons.

b. Different fluorophores (e.g. different emission wavelengths) for different targets using a single excitation (e.g. FRET probes which can be all excited using single excitation wavelength).

c. Different fluorophores for different targets using multiple excitation wavelengths with a single detector and a single emission filter. The single emission filter can be a wider bandwidth filter to allow the inclusion of larger portions of the emission signal from the various fluorophores (e.g. dyes) such as to obtain an equivalent sum of the emitted intensities.

d. Different fluorophores for different targets using multiple excitation wavelengths with multiple detectors and emission filters.

The various embodiments according to the present disclosure further allow for use of DNA binding dyes (e.g. fluorescent) like SYBR Green and FAM, or probes which bind to specific targets, primer attached fluorophores or other DNA binding probes. In further embodiments according to the present disclosure, multiplexing and quantification based on analysis of fluorescence versus temperature curves at various points during an amplification process (e.g. qPCR) other than just at the end of the annealing or extension phases are also provided.

The various embodiments according to the present disclosure further describe methods for obtaining multiple (e.g. different) quantifications (e.g. of amplicons) by using, for example, a single emission wavelength. It should be noted that the amplicons are obtained from a same assay containing different targets (e.g. DNA sequences or RNA sequences). It should also be noted that for the sake of clarity, the exemplary cases of two different amplicons obtained by amplification of two different targets is presented. Such exemplary cases of two amplicons should not be considered as a limitation of the presented embodiments but rather an exemplary case of the inventive concept as disclosed herein.

Amplification techniques of target genes or sequences are used to determine (e.g. quantify) an initial concentration of the target genes or sequences. As known by the skilled person, such initial concentration is referred to as, or identified by, the threshold cycle ($C_T$) which is defined by a detectable initial knee in the amplification curve corresponding to a detectable concentration of amplicons at an amplification cycle (e.g. a qPCR temperature cycle). A detected $C_T$ value can then be correlated to known prior concentrations to derive a concentration of the target genes thus completing the quantification process. Typically derivation of the $C_T$ value is performed after determining a successful (e.g. proper) amplification reaction which can be verified (e.g. verification process) by conducting, for example, an end point melting curve analysis on the amplicons or using positive and negative controls. In the exemplary case where two different amplicons are amplified (e.g. two different target genes), the end point melting curve analysis can determine whether a single specific amplicon is amplified, whether both amplicons are amplified or whether neither of the amplicons is amplified. In a successful amplification, also referred to as a proper reaction, both amplicons are amplified if the targets for both are present, and therefore one can proceed to find the $C_T$ value for each of the amplicons. In some cases one of the amplification reactions (e.g. creating amplicons) is a control reaction for which the $C_T$ value (e.g. concentration) is known. In other cases concentration of both targets are unknown. According to the various embodiments of the present disclosure, the unknown initial concentrations (e.g. $C_T$ values) can be found in both cases by analyzing the amplitude curve of the multiplexed reaction, also referred to as the sum amplitude curve, which relates to the total number of amplicons per detection cycle. In some cases, the analysis of the sum amplitude curve uses information obtained by analyzing of the melt curve (e.g. melting curve analysis). According to several embodiments of the present application, detailed analysis of the sum amplitude curve and the melt curve can be performed using powerful known mathematical functions and models which the person skilled in the art of signal processing, estimation theory and the like is well aware of.

When using intercalating dyes, the fluorescence intensity is about proportional to the length of the amplicon (e.g. the longer the amplicon the stronger the fluorescence intensity). According to some embodiments of the present disclosure, methods of analyzing the sum amplitude curve (e.g. corresponding to a total detected intensity) of the multiplexed amplicons is provided which enable to derive the $C_T$ and a corresponding amplitude curve for each of the multiplexed reactions. Such methods are also compatible for the case where primers with attached fluorophores are used. In other embodiment according to the present disclosure more dye molecules can be attached to one primer set vs. the other such as to obtain a higher fluorescence (e.g. amplitude) for one amplicons versus the other as a distinguishing feature of an associated amplification curve. As previously noted, methods according to the various embodiments of the present disclosure can be extended to multiple (e.g. more than two) amplicons. In some embodiments according to the present disclosure, the efficiency of the reactions can be different or designed to be different such as to limit a corresponding slope and shape of the amplification curve (e.g. of a given reaction) in order to facilitate detection of the various individual curves and corresponding $C_T$ values. In an exemplary embodiment, efficiency in amplification can be changed by using different primer concentrations for the different targets used in the multiplexed reaction such as to obtain individual target amplification curves with different slopes and shapes. Algorithms according to the various embodiments of the present disclosure can be used to separate the different amplification curves, which are superimposed onto each other (e.g. as per a single detection channel). According to further embodiments of the present disclosure, methods to obtain the total fluorescence of each reaction using the melt curve are provided.

FIGS. 1A-1D show the various possible relationships between the amplitude curves for the case of a multiplexed reaction using two target genes, each identified by a corresponding amplicon (amplicon1, amplicon2) respectively. It is assumed that the reaction is proper, such as the correct genes are amplified at an expected efficiency (e.g. amplitude slope), and verified, for example, via an end point melting curve analysis. For each of the four different cases represented by FIGS. 1A-1D, the total detected signal (e.g. total emitted fluorescence intensity detected via a single detection channel) is represented by the sum amplitude curve (sum), which corresponds to the sum of the individual amplitude curves (amplicon1) and (amplicon2). Furthermore, the derivative of the sum amplitude curve (sum), as well as its double derivative and its normalized double derivative are displayed for each of the four cases.

Figure 1B:
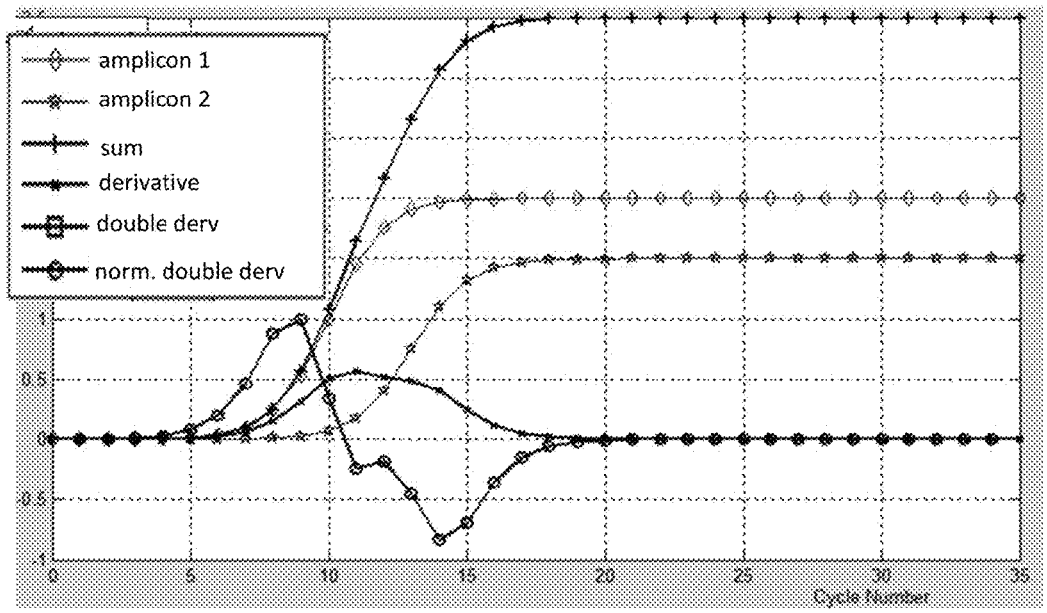
Figure 1C:
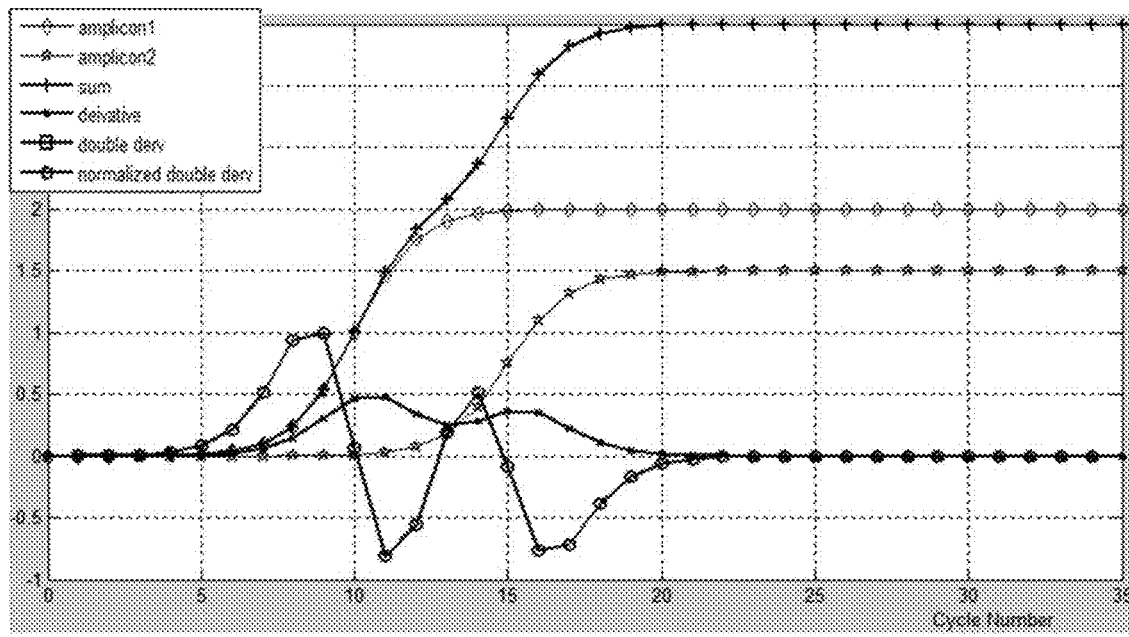
Figure 1D:
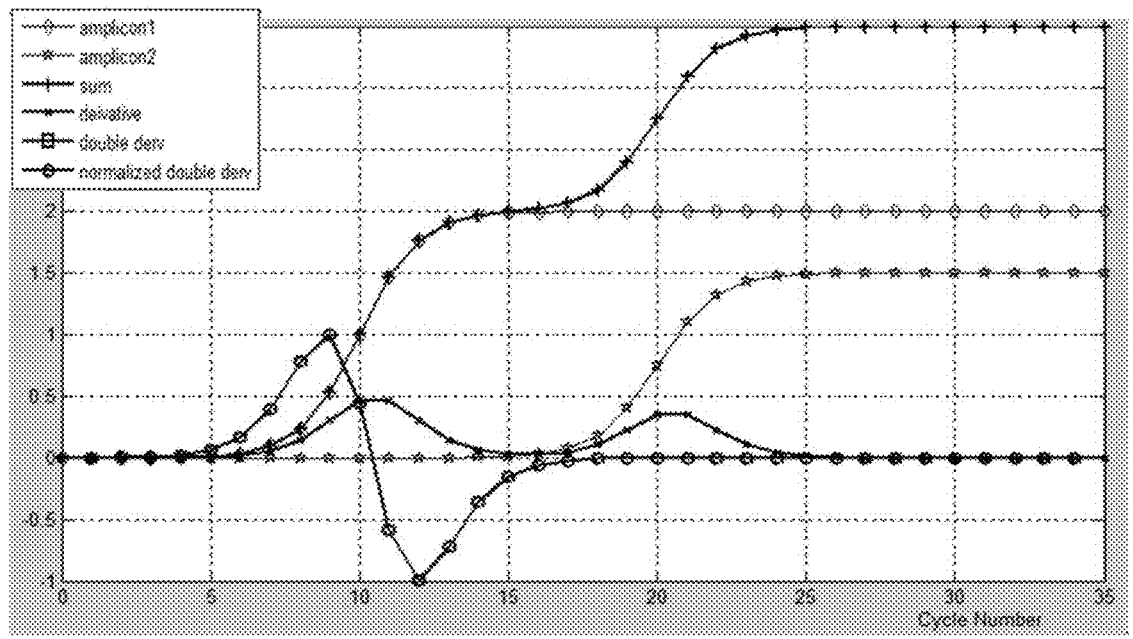

In the cases represented by FIGS. 1C and 1D, the amplifications of the two targets occur at differing cycle numbers making it relatively easy to determine the $C_T$ value for each of the reactions by using simple mathematical analysis, such as for example by using the double derivative of the sum amplitude curve, since there is very little overlap (e.g. of the amplification slope) of the two amplification curves as further displayed by the two distinct peaks in the derivative curves. In the cases represented by FIGS. 1C and 1D the slopes associated to the two amplicons are far enough apart such as to allow finding the $C_T$ value for each of the reactions by analyzing the flat portions and/or the portions with slope of the (sum) curve. For example, looking at the graph represented by FIG. 1D, at around cycle 8 a steep slope starts, which can indicate the start of a detectable amplification, and again at around cycle 19 a second steep slope starts, which can indicate the start of another amplification. By further examining, for example, the initial amplitude of each slope, one can determine that a single amplicon is being amplified during each slope (e.g. by verifying a slope amplitude representing an exponential amplification rate). Melting curve analysis can verify that both target amplicons are amplified. Although $C_T$ points are established, one still needs to associate these points to a specific amplicon of the multiplexed reaction. According to various embodiments of the present disclosure, a combination of sum curve analysis and melting curve analysis can provide said association.

In the case represented by FIG. 1A, the $C_T$ values are close, and therefore there are no additional peaks in the derivative and double derivative of the (sum) curve as compared to a single amplification curve of a single amplicon, thus rendering determination of the $C_T$ values difficult.

In the case represented by FIG. 1B, the $C_T$ values are close and there is a single peak in the derivative of the sum curve. However, a closer attention to the derivative curve shows an asymmetrical (bell) curve shape due to a skew of the two $C_T$ points. According to some embodiments of the present disclosure, the amount of asymmetry in the derivative curve can be used to determine the relative position of the two $C_T$ points. Also in the case represented by FIG. 1B, the double derivative has more peaks than the amplification curve of a single amplicon which further indicates a skew of the two $C_T$ points.

According to the various embodiments of the present disclosure, methods are provided such as to enable derivation of the $C_T$ values and association to specific amplicons of a single detection channel multiplexed reaction for all of the possible cases (e.g. as represented by FIGS. 1A-1D), by mathematically analyzing the sum amplitude curve and/or the melt curve.

Figure 2:
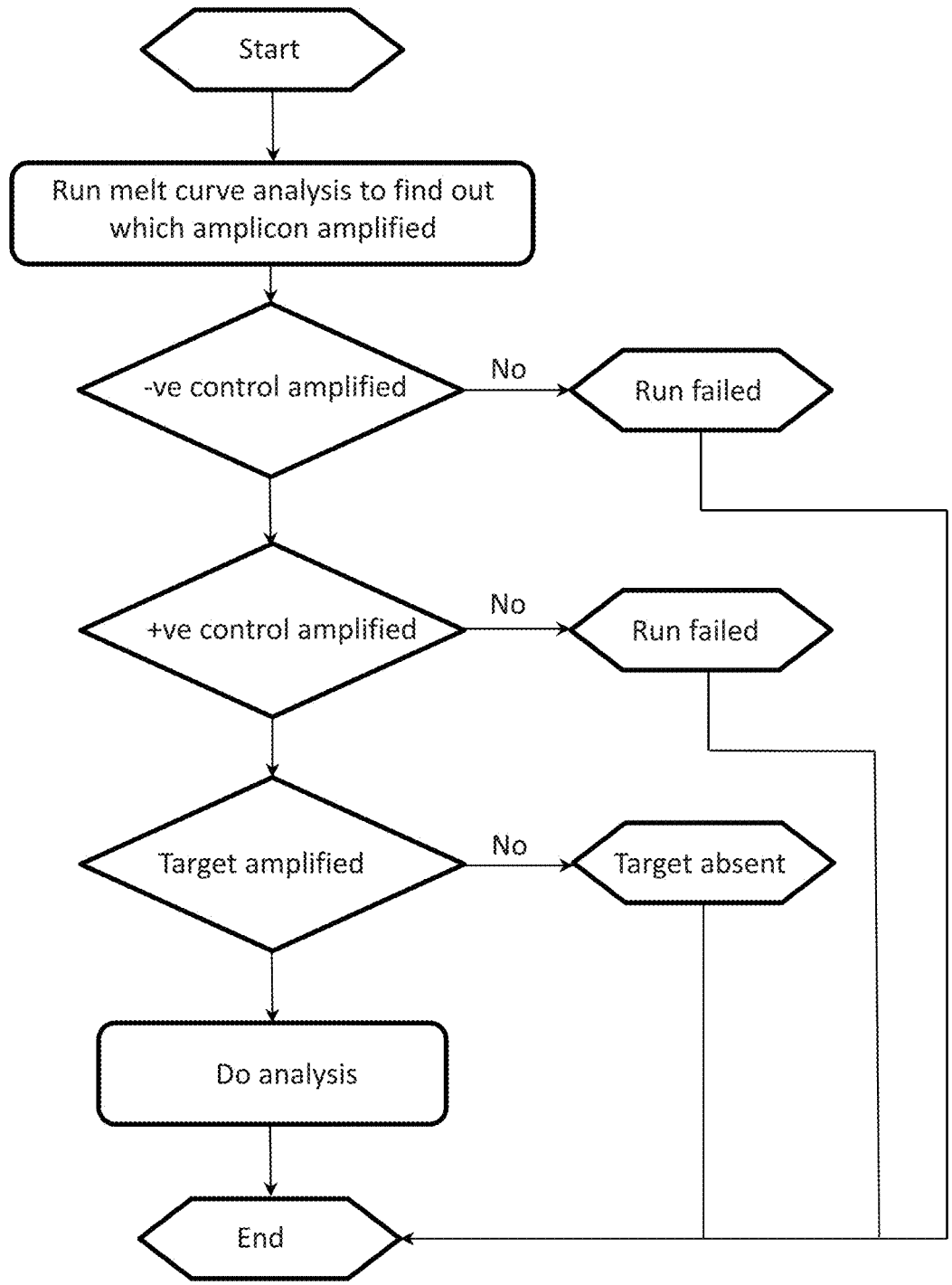
FIG. 2 shows a flowchart of an algorithm according to the present disclosure for a single color detection multiplexed reaction.

According to an embodiment of the present disclosure, FIG. 2 shows a flowchart of an algorithm for a single color detection of one target with positive and negative controls. Such as in a case of a qPCR reaction, it is here assumed that the reaction is run in a sequence of repeated cycles, wherein further amplification may be obtained with each run of the cycle. The proposed algorithm provides a method to derive the concentration of the multiplexed target and positive control via detection of the corresponding $C_T$ values irrelevant of their relative distance. The algorithm of FIG. 2 performs the following steps:

1. At the end of the reaction (e.g. all the cycles) run a melting curve analysis which yields the following:
    a. Which amplicons did amplify, as each amplicons has a different melting temperature ($T_M$) per design.
    b. What was the amplitude of the fluorescence for each amplified amplicon assuming it reached a plateau level. It also gives the amplitude, which is at the end of the cycles, even if it did not plateau.
    c. The background fluorescence, for example by observing the detected level of fluorescence at the end of the melting curve analysis.
    d. Quality of amplification to some extent, for example by contrasting the observed shape of the melt curve and an expected shape based on known parameters.
2. If negative control did amplify then reaction has failed.
3. If positive control did not amplify then the reaction has failed.
4. If target did not amplify then target is absent not detectable. Report this and go to End.

Figure 10:
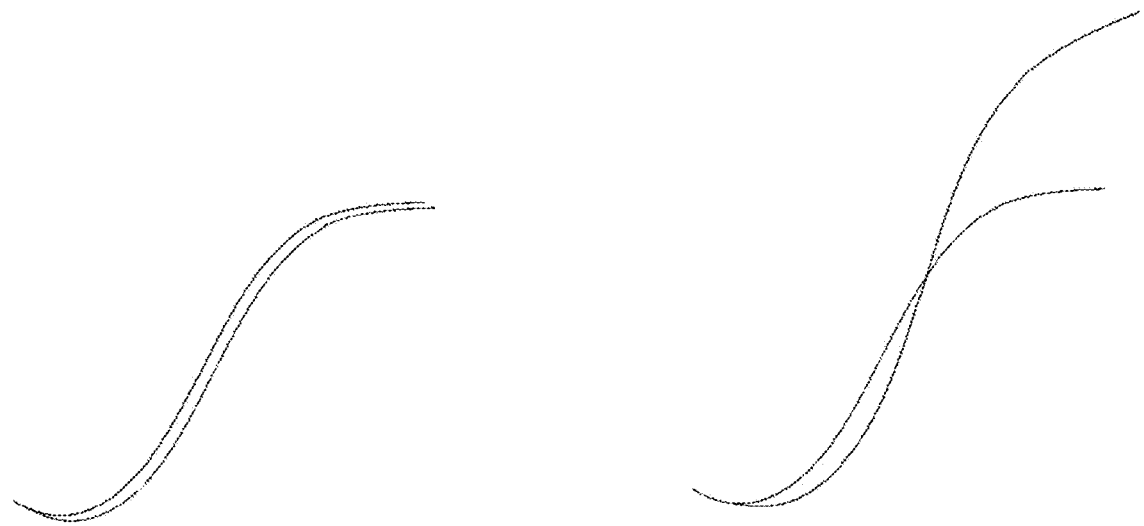
FIG. 10 shows error in minimum cumulative point wise distance between two normalized and two non-normalized curves.

5. Otherwise do analysis of the sum amplification curve:
   a. Analyze the sum amplitude curve to look for peaks:
      i. Using derivatives and double derivatives of the sum amplitude curve.
      ii. Using various peak detection algorithms known in the art, such as for example CFAR type detection algorithms (e.g. as used in radar theory).
   b. If enough peaks are detected with confidence, then the $C_T$ values are sufficiently distant:
      i. Derive the $C_T$ values of both the amplicon and the positive control. To be noted that the $C_T$ value of the positive control may be known in advance. The $C_T$ value of positive control can be made to be at later cycles, for example, it can be put after the maximum $C_T$ which can be accepted for clinical relevance or acceptance of the reaction. This simplifies finding the $C_T$ value of a valid amplification as the positive control will not affect the determination of the $C_T$ value of the target. The amplitude of positive control at or after the plateau phase can also be limited by limiting, for example, the amount of primers.
      ii. Optionally verify the derived $C_T$ values using the distance-based method as described below. (step c.vi.)
   c. If not enough peaks are detected, then the $C_T$ values are near (assuming amplifications with efficiency as expected/specified):
      iii. Optionally normalize amplitudes of target and positive control using the amplitudes obtained from the melting curve analysis.
         (Amplitude may be normalized such as to assume same amplitude for each of the individual amplitude curves as per reference data used to correlate $C_T$ points to known concentrations, otherwise accuracy can be degraded as shown in FIG. 10). Use the total fluorescence intensity (e.g. amplitude) and the points where the melting occurs for each amplicon to estimate the maximum of each individual fluorescence curve.
      iv. Do a skew analysis on peaks to estimate a $C_T$ difference of the two amplicons. Amplitude information of both amplicons (e.g. target and positive control) as obtained via the melting curve analysis can be used for this step.
      v. Assume different values of $C_T$ for target amplification and for positive control amplification and based on the assumed different values generate the corresponding sum amplitude curves. Running various experiments and storing the corresponding data or using mathematical models or a combination of both can obtain these $C_T$ values. If the $C_T$ value of the positive control is known, then it can be fixed and the sum amplitude curves can only be different by the assumed $C_T$ values of the target amplification.
      vi. Take the difference of absolute values between the sum amplitude curves (e.g. absolute or squared) based on the assumed $C_T$ values and the actual measured sum amplitude curve. Analyze the result and select the $C_T$ value (or values in the case where positive control value is not known), which is estimated to be the closest to the actual value. Optionally the $C_T$ value corresponding to a minimum distance can be selected as the actual value. Optionally the shape of the distance curve surface/function may be taken into account.
6. End.

Using the algorithm represented by FIG. 2 to implement a single color detection method to amplify a target with both positive and negative controls is attractive as it allows a reliable detection in POC instruments and in commercial machines.

In multicolor machines (e.g. having multiple detectors), this multiplexing technique (e.g. FIG. 2) can be used for each color thus enabling the following:
- Have positive and negative control on one color and use other colors separately for detection of other targets
- Have positive and negative control for each color and target
- Increase the number of amplicons, which can be detected by two or three fold. (later we show how to increase this even further)

Figure 3:
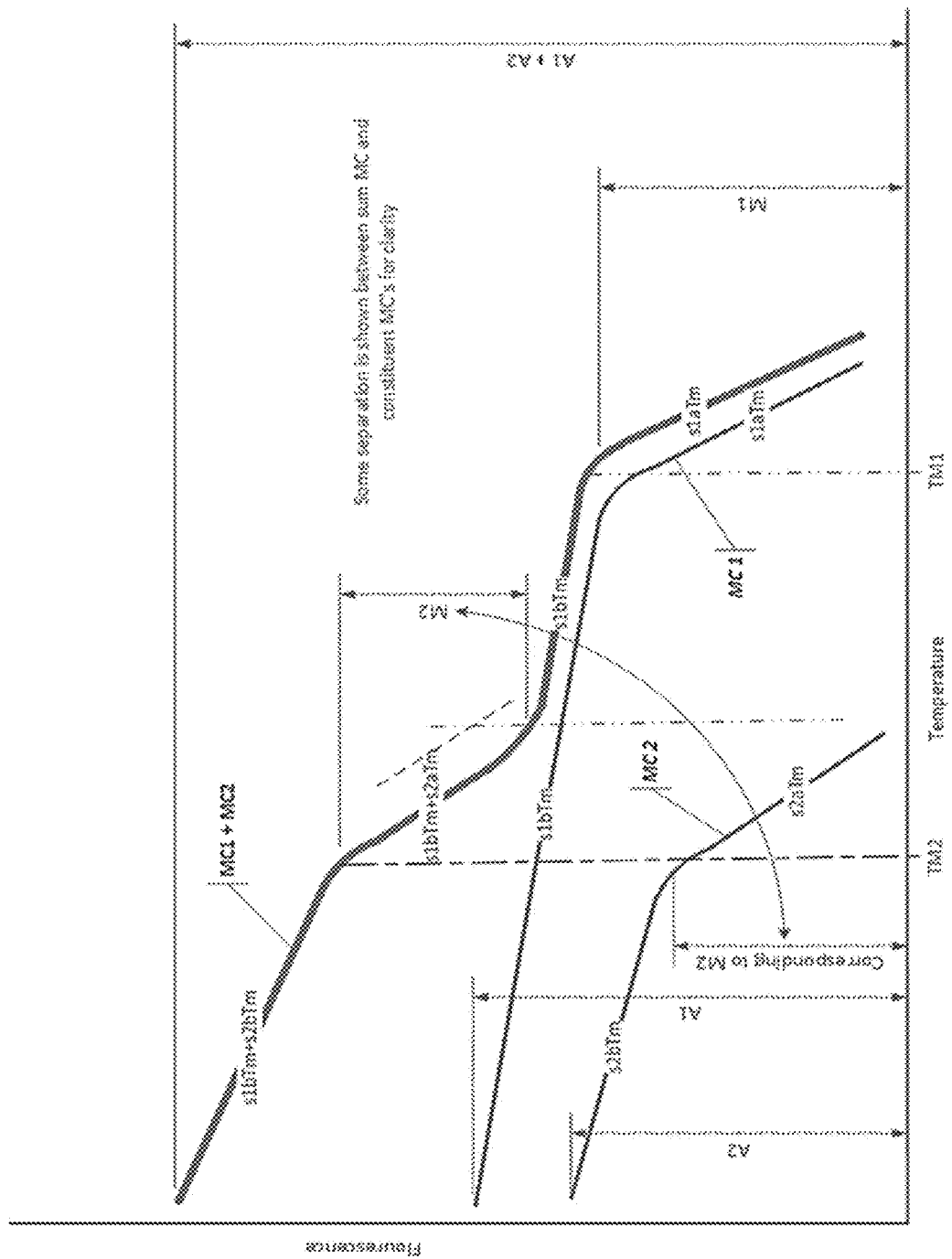
FIG. 3 shows an exemplary sum melt curve of two amplicons and its two constituent melt curves associated to each of the amplicons.

According to an embodiment of the present disclosure a method for finding amplitude of amplification curves via sum melt curve analysis and finding constituent melt curves from the observed sum melt curve via a single channel detection is provided. FIG. 3 shows an exemplary sum melt curve (MC1+MC2) corresponding to two amplicons (a1, a2) generated through an amplification process. Based on this sum melt curve it is desired to extract its constituent curves (MC1) and (MC2) which are further shown in FIG. 3. The sum melt curve changes slope appreciably near (TM1) and (TM2) which are the melting temperatures of amplicons (a1) and (a2) respectively. According to the observed sum melt curve (MC1+MC2), the slopes at various regions of the curve are known and can be associated to the slopes of the various regions of the individual curves (MC1) and (MC2) as seen in FIG. 3. By defining:

s1bTm: slope of (MC1) before its melt temperature (TM1)
s1aTm: slope of (MC1) after its melt temperature (TM1)
s2bTm: slope of (MC1) before its melt temperature (TM2)
s2aTm: slope of (MC1) after its melt temperature (TM2)

based on the observed sum melt curve (MC1+MC2) and as depicted in FIG. 3, the following expressions are known:
(a) s1bTm+s2bTm
(b) s1bTm+s2aTm
(c) s1bTm
(d) s1aTm These four independent expressions therefore allow to determination of each of the two slopes associated to the constituent melt curves (MC1) and (MC2).

Assuming the amplitudes of the constituent melt curves (MC1) and (MC2) are (A1) and (A2) respectively, then based on the observed single channel sum melt curve, the following amplitudes are known:
(e) A1+A2
(f) M1
(g) M2

Using well known mathematical techniques, the skilled person will know how to estimate (A1) and (A2) by using the relationship of (M1, M2) with (TM1, TM2).

Finding amplitudes of the various constituent melt curves (e.g. of the sum melt curve) as per the method described above and depicted in FIG. 3, allows to correlate amplitude curves (e.g. $C_T$ values) to specific amplicons, by using for example the relative amplitudes obtained via the sum melt curve analysis provided above (e.g. FIG. 3) and the amplitude curves obtained from the sum amplitude curve as per any one of the various embodiments of the present disclosure. The melt curves can associate an amplicon to a relative amplitude (e.g. via known melt temperature), which can then be correlated to an amplitude of an amplitude curve. For example, and in relation to FIG. 3, amplitude (A2) which corresponds to amplicon (a2) is relatively larger than amplitude (A1) of amplicon (a1). Therefore, if analysis of the sum amplitude curve corresponding to generation of amplicons (a1, a2), yields in two separate $C_T$ values, the larger value will correspond to amplicons (a2) and the smaller value to amplicon (a1).

In some cases the slope of the amplitude curves in the plateau phase (e.g. minimal amplification region subsequent to the exponential phase) may be difficult to determine. Therefore, according to an embodiment of the present disclosure the exponential phase only of the assumed amplitude curves (e.g. FIG. 4 later described) may be used for the analysis (e.g. step 5 of the algorithm). Similarly, a phase of an amplitude curve where no amplification is detectable (e.g. relatively flat region of the curve) according to an assumed and/or the actual amplitude curve, can be excluded from the analysis. Such technique of eliminating regions (e.g. phases) of the curve containing minimal information from the analysis step can give a better and more robust analysis result. It should be noted that the region of interest for the analysis is typically the area of exponential amplification of an amplitude curve which is at the vicinity of a corresponding $C_T$ point. Assuming that the amplification is proper (e.g. maximum efficiency and expected amplicons generated), then it is expected that the amplitude change (e.g. amplification) at the vicinity of a $C_T$ point follows an exponential curve, as at the vicinity of a $C_T$ point amplification occurs at a rate of $2^N$ where N is a number associated to an amplification cycle. The skilled person will not need further explanation on this and will appreciate the benefits of using/analyzing the relevant regions (e.g. slopes) of the amplitude curves in order to detect the various $C_T$ points.

Figure 4:
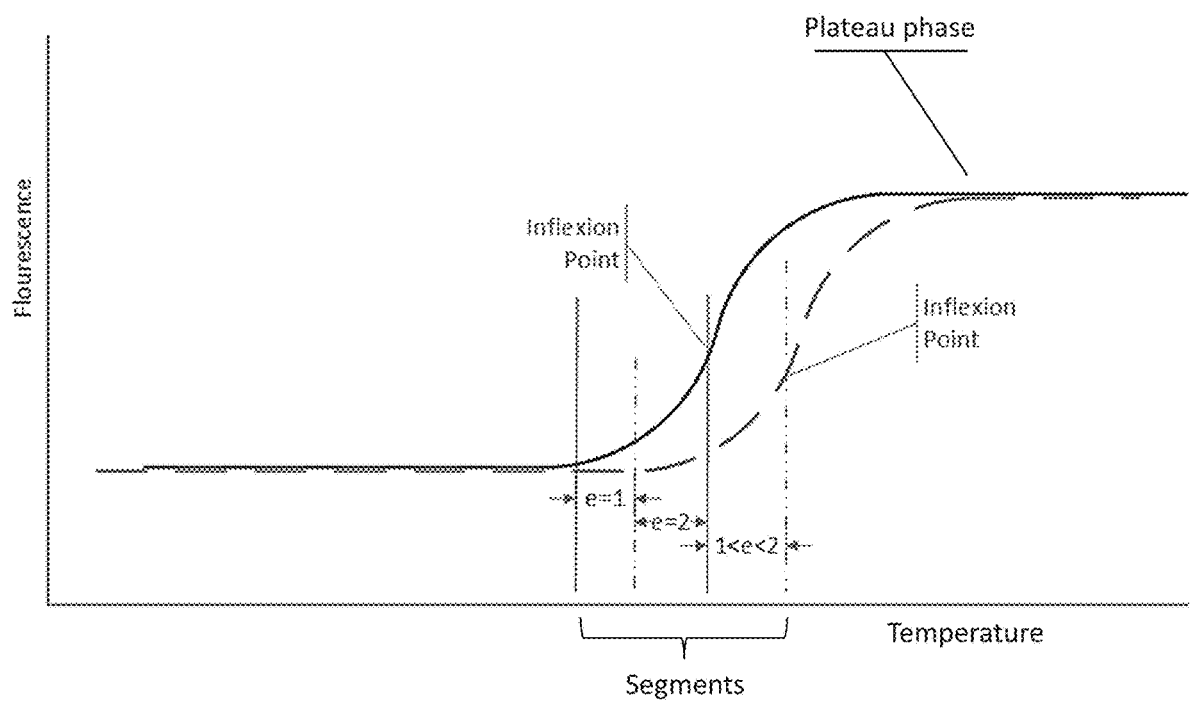
FIG. 4 shows exemplary amplification curves of two amplicons with threshold cycle ($C_T$) points close to each other.

FIG. 4 shows exemplary amplification curves of two amplicons with $C_T$ points close to each other. As per prior paragraphs, by observing and analyzing a slope (e.g. represented by an efficiency e of the reaction) in FIG. 4) of the sum amplification curve it is possible to directly determine the $C_T$ point of each amplicon. By tracking the exponential phase only of the sum amplitude curve and assuming that each reaction worked properly (e.g. amplified at the proper rate), each of the constituent amplitude curves can be represented as shown in FIG. 4. When the first amplicon starts to be detected above a corresponding $C_T$ value while the second amplicon is not being detected, the efficiency e is close to 1 (e.g. one amplicon amplified properly) as shown in the first segment of FIG. 4. When the second amplicon crosses its corresponding $C_T$ value, two proper amplification reactions are detectable with each being in a corresponding exponential phase. Thus in the second segment of FIG. 4 the corresponding efficiency (e.g. slope) value is close to 2, showing that both amplifications are in exponential phase. Finding these two initial segments are enough to find the $C_T$ value of each of the two amplicons, based on the fact that an exponential phase of either amplicon has an efficiency (e.g. slope) contribution to the observed sum amplitude curve of approximately 1. In the case where the two $C_T$ values are the same, then the two segments are merged and a single segment with an efficiency value of approximately 2 is observed. In the third segment the efficiency of amplification of one or both amplicons starts decreasing, thus the total observed efficiency also starts decreasing from the value of approximately 2 as an amplification starts approaching a plateau phase. In the third segment the efficiency value (e.g. slope) changes from a value of less than 2 to 0 in the case where both amplifications enter the plateau phase.

The technique disclosed above to detect $C_T$ values based on the slope of the sum amplitude curve is easily adaptable to cases where $C_T$ values are far apart by easy extension of this technique. This technique is robust since it seeks to find the exponential phase of amplification which occurs during the parts of reaction (e.g. of one of the constituent amplicons) where efficiency is close to 1 and is thus not dependent on the amplification curve taking other shapes due to, for example, limited reagents availability during the later stages of the reaction.

According to a further embodiment of the present disclosure, the disclosed algorithm for a single color detection of one target with positive and negative controls can be further extended to include more than two targets while keeping both the positive and the negative controls. As for the single target case, the peaks in derivative and double derivative curves and the amplitude (e.g. as detected via the melting curve analysis) can be used to separate the amplitude curves for each of the multiple amplicons from the sum amplitude curve (e.g. steps 5.a. and 5.b. of single amplicons algorithm).

For the case of multiple targets with one positive control and one negative control, same algorithm as used for the case of single target can be sued, with the exception of steps 5.c.v. and 5.c.vi. which may be replaced by the following steps:

> For each amplified amplicon assume some $C_T$ values based on prior analysis results.
> For all assumed $C_T$ values
> Generate all or part of the sum amplitude curve
> Find the distance over all or portion of the generated sum amplitude curve to the measured sum amplitude curve
> (e.g. may calculate distance over a portion such as the exponential phase of the curves)
> End for
> Select the most probable $C_T$ values (e.g. which minimize the distance)

According to some embodiments of the present disclosure, the proposed multiplexing algorithm can be used to increase the multiplexing capability of instruments used for amplification of target genes which have multiple optical detection channels. For example by implementing such algorithm in a 4 channel instrument, the instrument can be upgraded to detect 12 targets with 3 targets multiplexed per color using the disclosed multiplexing algorithm. In the case where 4 targets are multiplexed per color using the disclosed algorithm, then the same 4 channel instrument can be upgraded to detect 16 targets. The skilled person will know that such instruments perform all or part of their data analysis of the observed/detected emitted intensity (e.g. fluorescence) based on algorithms implemented in a combination of software and/or firmware code embedded within a processor-controlled hardware of the instrument, such as, for example, the processor-controlled hardware depicted in FIG. 11. Such algorithms perform upon a digital representation of the observed/detected emitted intensity read into a memory module accessible by (or part of) the processor-controlled hardware. Such digital representation can be obtained, for example, via an analog to digital converter module which converts an analog signal representing the observed/detected emitted signal to an equivalent digital representation. The skilled person will realize the possible upgrade to all or portion of such software and/or firmware to include the proposed single channel multiplexed algorithm. In alternative embodiments according to the present disclosure, data observed/detected by an instrument in its standard configuration may be analyzed off-line using the proposed multiplexing algorithm such as to not disturb an existing instrument. In this case the proposed multiplexing algorithm may be entirely implemented in software and/or firmware running on a computer and/or processor-controlled hardware.

Figure 11:
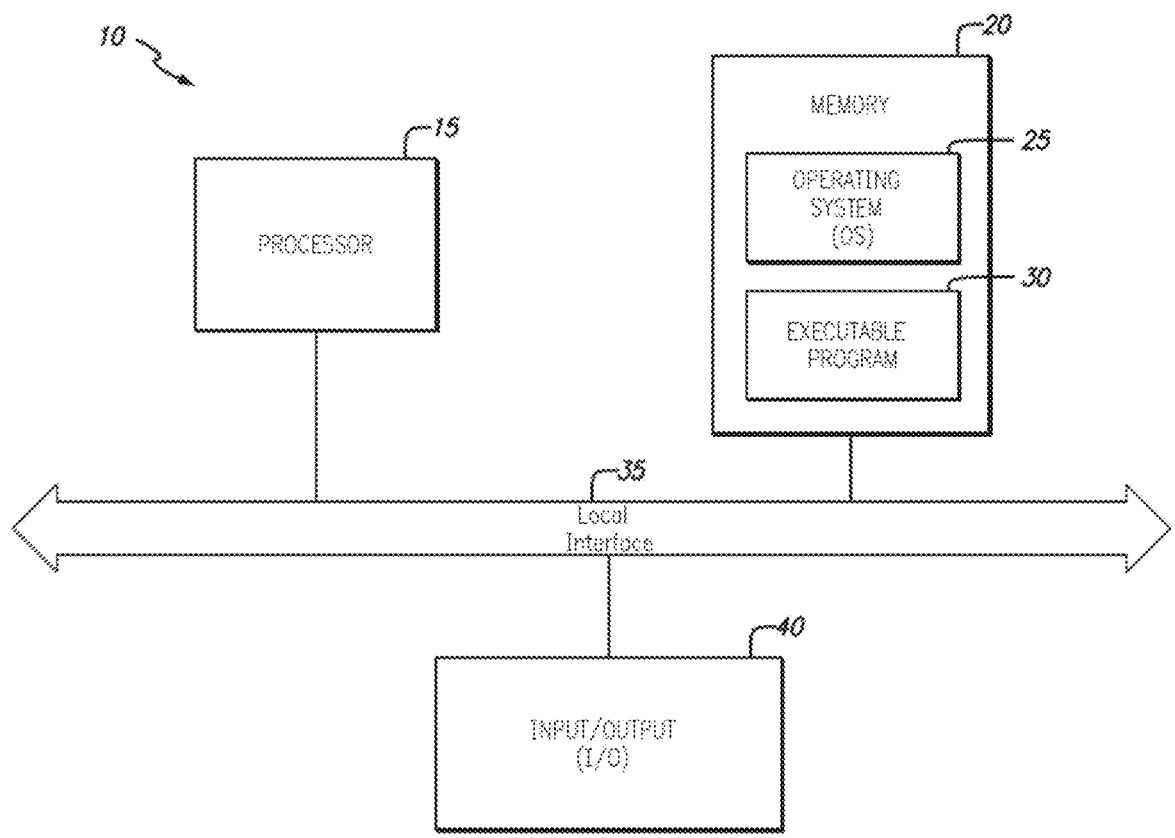
FIG. 11 is an exemplary embodiment of a processor-controlled hardware used in a single color detection multiplexed amplification reaction.

FIG. 11 is an exemplary embodiment of a processor-controlled hardware (10) (e.g. a computer system) as discussed in the previous paragraphs. This processor-controlled hardware comprises a processor (15), a memory bank (20), a local interface bus (35) and one or more Input/Output devices (40). The processor may execute one or more instructions related to the implementation of the discussed mathematical analyses and related algorithms for quantification and verification of the amplification process and as provided by the Operating System (25) based on some executable program stored in the memory (20). These instructions are carried to the processors (20) via the local interface (35) and as dictated by some data interface protocol specific to the local interface and the processor (15). It should be noted that the local interface (35) is a symbolic representation of several elements such as controllers, buffers (caches), drivers, repeaters and receivers that are generally directed at providing address, control, and/or data connections between multiple elements of a processor based system. In some embodiments the processor (15) may be fitted with some local memory (cache) where it can store some of the instructions to be performed for some added execution speed. Execution of the instructions by the processor may require usage of some input/output device (40), such as inputting data from a file stored on a hard disk (e.g. data representing a sum amplitude and/or a sum melting curves), inputting commands from a keyboard, outputting data to a display, or outputting data to a USB flash drive. In some embodiments, the operating system (25) facilitates these tasks by being the central element to gathering the various data and instructions required for the execution of the program and provide these to the microprocessor. In some embodiments the operating system may not exist, and all the tasks are under direct control of the processor (15), although the basic architecture of the processor-controlled hardware device (10) will remain the same as depicted in FIG. 11. In some embodiments a plurality of processors may be used in a parallel configuration for added execution speed. In such a case, the executable program may be specifically tailored to a parallel execution. Also, in some embodiments the processor (15) may execute part of the quantification and/or verification, and some other part may be implemented using dedicated hardware/firmware placed at an Input/Output location accessible by the target hardware (10) via local interface (35) (e.g. dedicated PCB boards for digitizing a detected amplification signal). The processor-controlled hardware (10) may include a plurality of executable program (30), wherein each may run independently or in combination with one another.

As known by the skilled person, when intercalating dyes are used for detection of an amplification reaction, the amplitude of the fluorescence (e.g. associated with the intercalating dyes) will change with the amplicon length. In the case where sequence specific probes (e.g. bind only to specific targets) are used to monitor an amplification reaction, intercalating dyes can be added to the reaction (e.g. the assay comprising the various reagents) without affecting the monitoring efficiency of the amplification reaction and provide the advantage of allowing a melting curve analysis. The skilled person will know that some sequence specific probes are not compatible with a melting curve analysis thus addition of an intercalating dye can be beneficial in, for example, performing the disclosed single color multiplexed reaction detection algorithm.

For a probe-based reaction, the number of fluorophores on the probes can be different for different amplicons. The reporter molecules can be different but emit in the same wavelength or in two wavelengths that are substantially the same, such as a same detector can detect both wavelengths with a sufficiently high efficiency. For example FAM, Eva Green and SYBR Green dyes have similar, or substantially same, emission spectra. Such dyes can be used for target specific probes and still allow multiplexed detection of several targets using the disclosed single color multiplexed reaction detection algorithm. This, for example, can allow probe-based detection in a same detection channel. Thus it is possible to get specificity of probes and quantification of different targets using a single detection channel.

The single color detection algorithm disclosed is also compatible for a multiplexed reaction where different spectra dyes are used. In this case the relatively wide emission spectrum of the various dyes is used to detect all or a portion of the emission spectrum through, for example, a same absorbance filter. For example Texas Red will have a greater portion of its spectrum going through an absorbance filter with a cut-off wavelength of 520 nm (e.g. passes wavelengths above 520 nm) than, for example, SYBR Green.

In the case where FRET probes are used, which have FAM as acceptor dye (e.g. single excitation wavelength) and different donor dyes (e.g. different emission spectra), the amplitude of the different amplicons generated through a multiplexed reaction can be different while being able to use a single excitation wavelength. Distinction in amplitude of the different amplicons can facilitate correlation of the amplicon specific amplitudes detected via a melting curve analysis, and the $C_T$ points detected from the sum amplitude curves as per the analysis disclosed in the single color multiplexed reaction detection algorithm of this disclosure.

Figure 8:
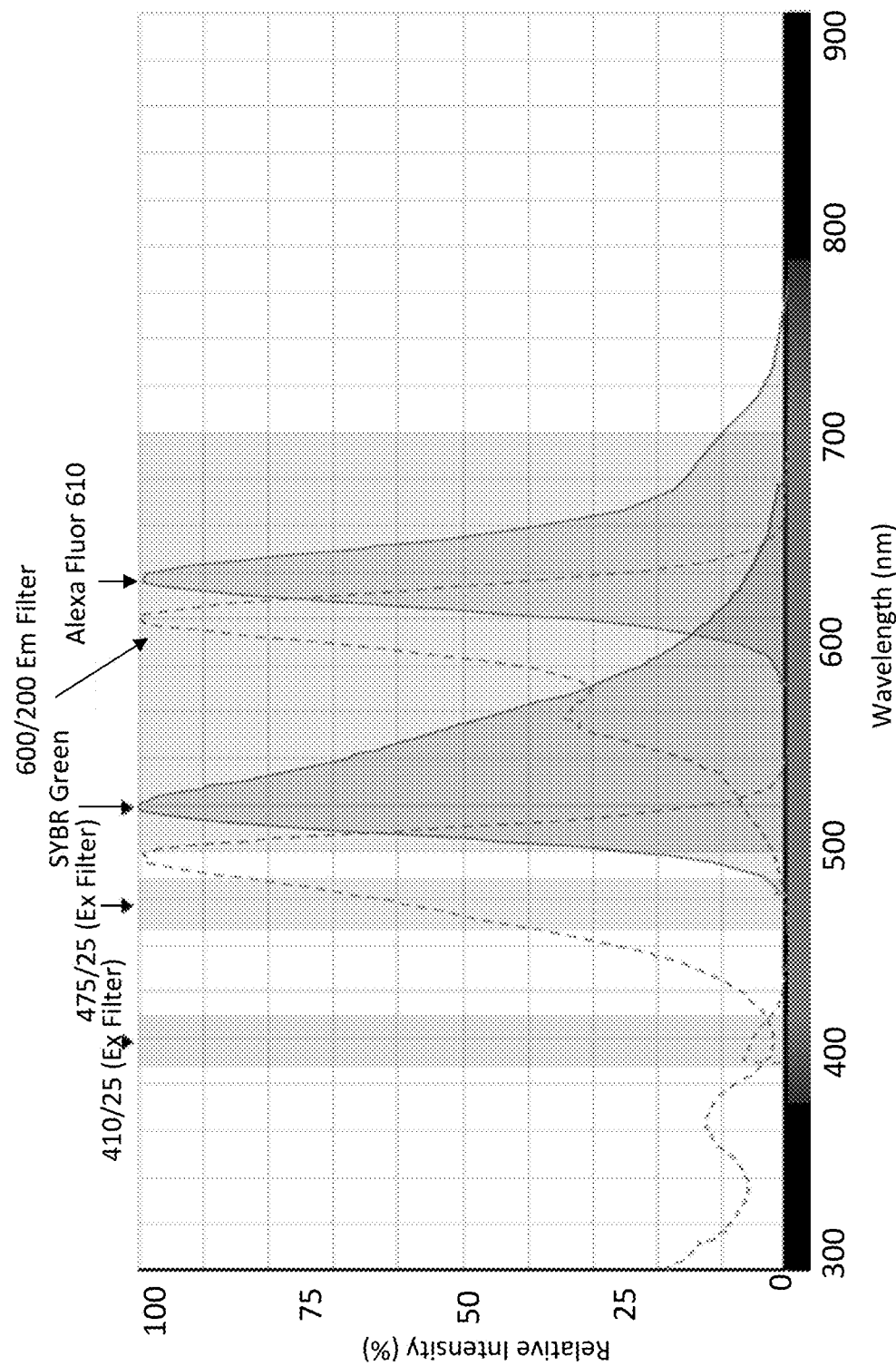
FIG. 8 shows an excitation and emission spectra of SYBR Green and Alexa Fluor dyes, together with a wide detection filter used to detect portion of the emission spectra of both dyes.

In some cases different excitation wavelengths are used with different probes designed to emit at different wavelengths. Using different emission wavelengths will yield different amplicon amplitudes for various probes which can be used to further differentiate the various amplicons based on amplitude. For example Alexa Fluor 610 is minimally excited by wavelength of 475 nm (475/25 blue filter) so a blue LED (or a blue filter) can be used to excite SYBR Green only, which yields in detection of amplicons specific to probes with SYBR Green. On the other hand, a wavelength of 410 nm can excite both the SYBR Green and the Alexa Fluor dyes, and thus yielding in detection of amplicons specific to probes with both SYBR Green and Alexa Fluor. As depicted in FIG. 8, which was taken from a webpage, retrieved on Aug. 2, 2013, a detection filter (e.g. 600/200 Em Filter) with a wide enough bandwidth covering a wavelength ranges of [500 nm, 700 nm] can be chosen to detect emission spectra (e.g. portion of) corresponding to both the SYBR Green and the Alexa Fluor dyes. Detecting emission of both amplicons with one excitation source and then emission of only one amplicon with a second excitation source can allow determining of the emission of each amplicon. As depicted by FIG. 8, one can multiplex using a single detector but different excitation sources and still capture a large portion of the spectrum of dyes in contrast to using bandpass filters specific to each of the emission wavelengths. One can get the amplitude information by getting melting curves with multiple excitation sources in series to get the amplitudes of both. This means select an excitation source, run a multiplexed reaction and analyze reaction using provided algorithm, then select a different excitation source, run a multiplexed reaction and analyze reaction using same algorithm. Multiplexing of the excitation source thus allows increasing detection capability of an instrument for each detection channel.

To control the amplitude of an amplicon the primers can be limited. For example the positive control can have limited primers so that it plateaus close to a designed value. As previously mentioned, controlling the amplitude of an amplicon in a multiplexed reaction can facilitate detection of a corresponding $C_T$ value as per the disclosed single color multiplexed reaction detection algorithm.

The initial period of a reaction, where none of the amplicons in the amplification has entered an exponential phase (e.g. corresponding to amplitude curve region with steepest slope), can be treated as background fluorescence and can be subtracted from the total fluorescence waveform (e.g. sum amplitude curve).

Figure 5A:
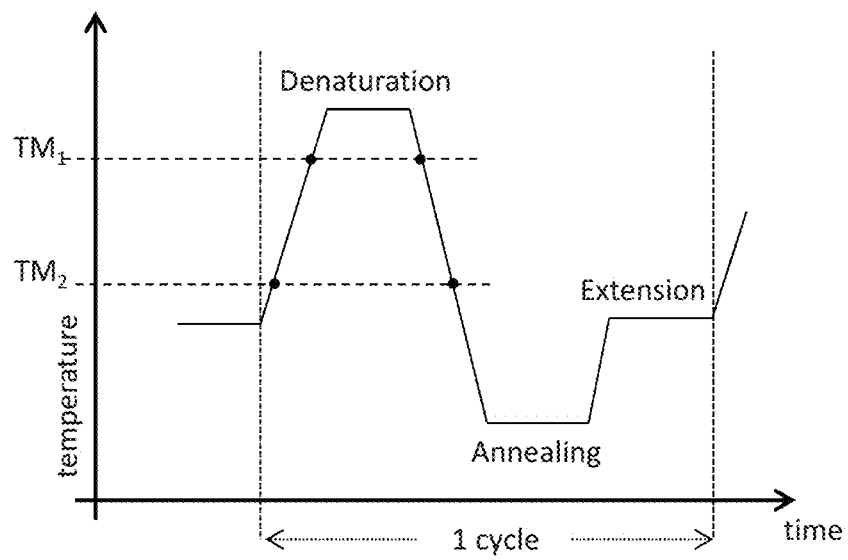
FIGS. 5A and 5B show a typical three step and two step respectively temperature cycle of an amplification process and melting temperatures associated to amplified amplicons.
Figure 5B:
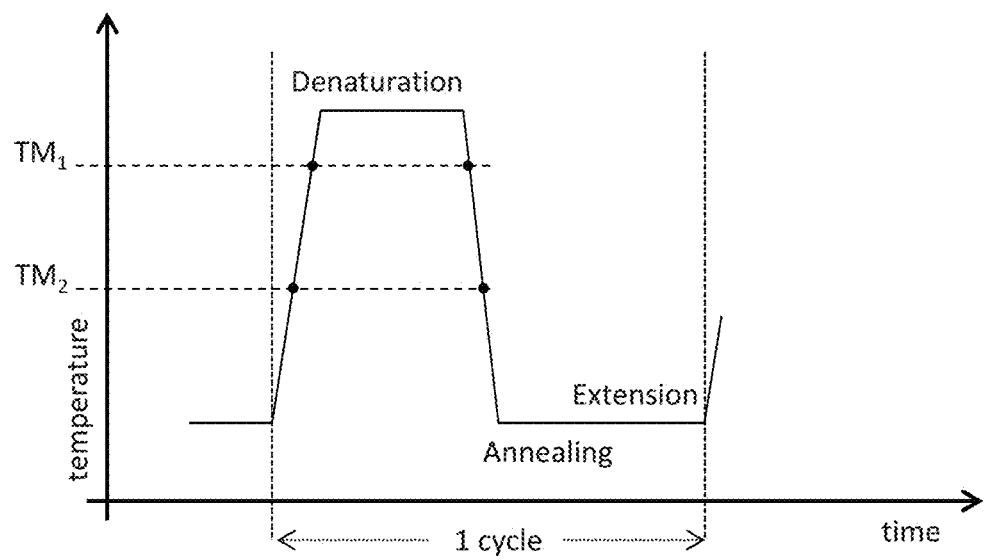

According to one embodiment of the present disclosure, partial melting curve analysis is performed during each cycle of an amplification reaction, such as for example a multiplexed qPCR reaction. Such cycle by cycle partial melting curve analysis can determine the quantification of various amplicons during the course of the amplification reaction. FIGS. 5A and 5B show a typical cycle (e.g. temperature cycle) of an amplification process, whereby a temperature of an assay containing genes to be amplified is subjected to various levels corresponding to a denaturation phase, an annealing phase and an extension phase of a DNA sequence associated to the gene. As represented in FIG. 5A, the temperature levels for the annealing and extension phases are different whereas in the case of FIG. 5B these levels are equal. The skilled person will need no additional information on the inner working of an amplification process and the relevance of the various temperature levels as related to the three main phases of the amplification process. In a typical amplification process, the transition regions from one temperature level of a cycle corresponding to a phase of the cycle to another temperature level corresponding to a different phase of the cycle is not critical to the amplification process and is typically a function of characteristics associated to the heating/cooling elements and a chamber of an associated amplification process instrument.

Figure 6A:
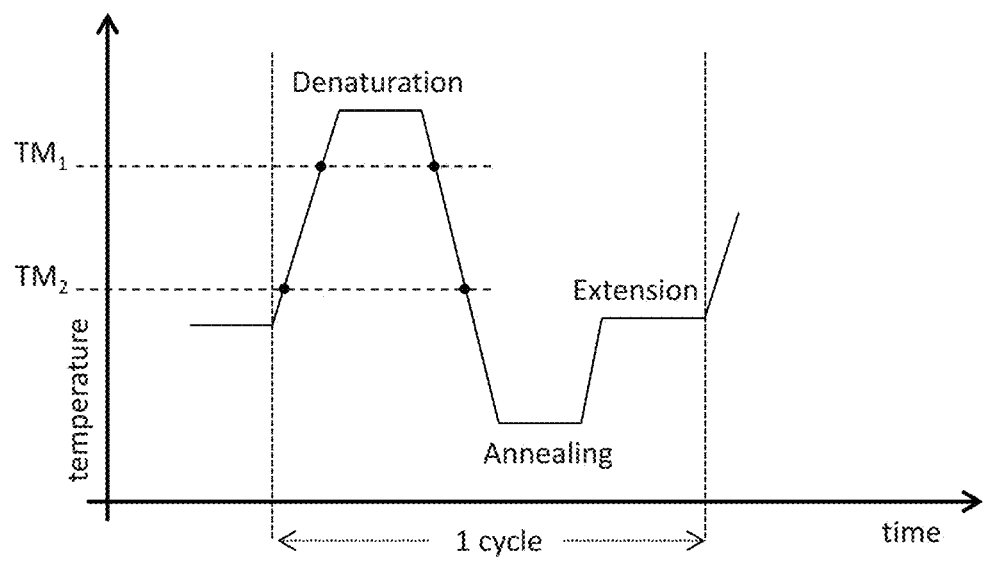
FIG. 6B shows an embodiment according to the present disclosure of a modified temperature cycle of the three step cycle depicted in FIG. 6A, wherein segments of a transition region around various melting temperatures of amplicons are modified to have less steep slopes, the transition region being a ramping down of the temperature of the cycle.
Figure 6B:
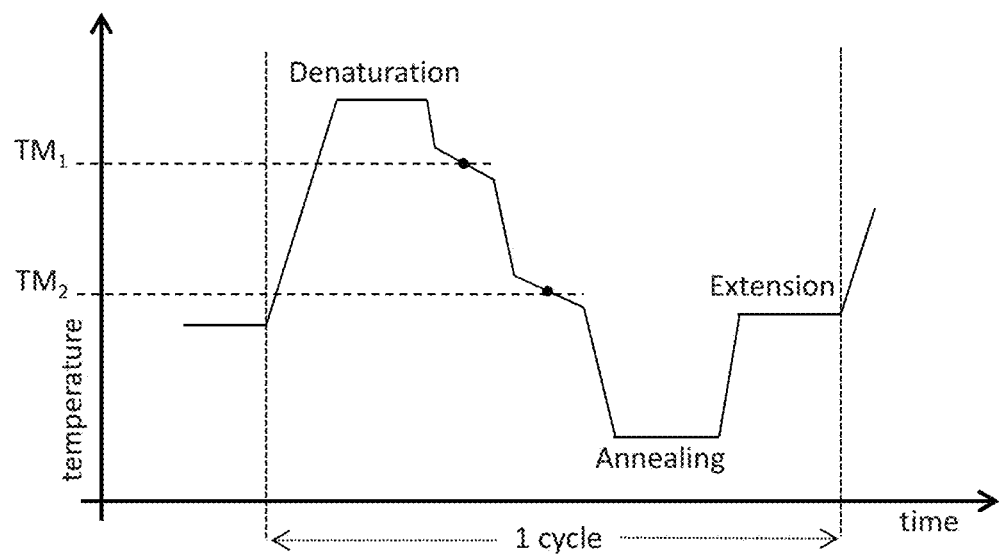
Figure 7A:
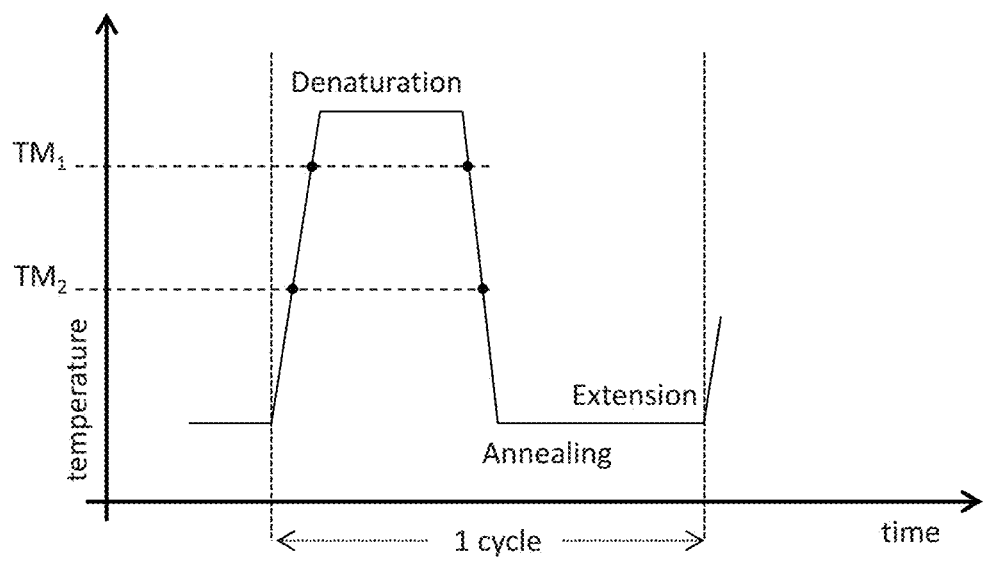
FIGS. 7A and 7B are equivalent to FIGS. 6A/6B for a case of a two step cycle and wherein the transition region is a ramping up of the temperature of the cycle.
Figure 7B:
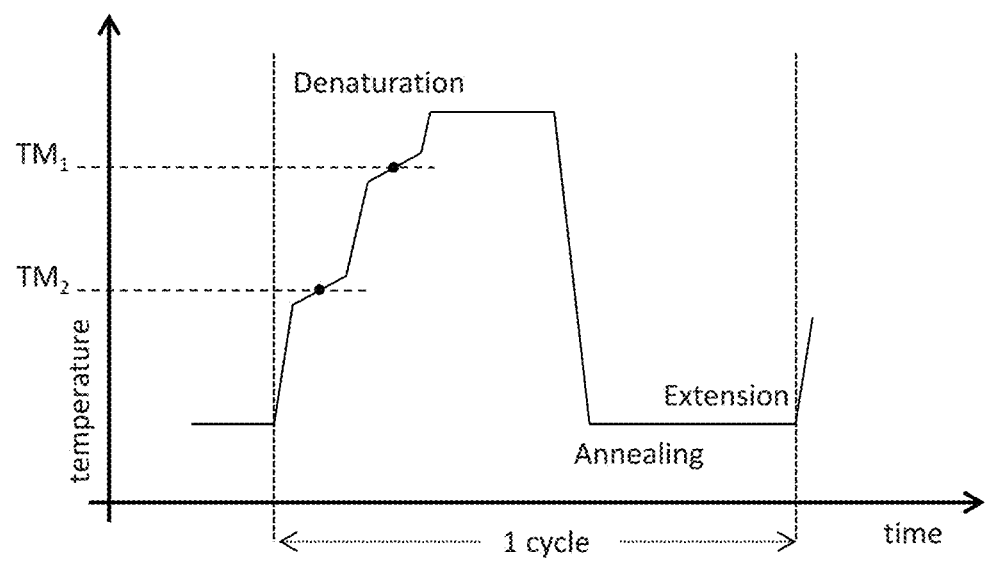

FIGS. 5A and 5B show melting temperatures (TM1, TM2) associated to two different amplicons being amplified. As known by the skilled person these melting temperatures are known a priori and set per design of the target specific primers used in the reaction. According to various embodiments of the present disclosure, melt analysis of the various amplicons of the amplification process, for example as associated to the melt temperatures (TM1, TM2) can be performed at the vicinity of these temperatures, either during a region of ramping up of the temperature or a region of ramping down of the temperature in the cycle. In some embodiments according to the present disclosure, the cycles can be slowed down such as to allow better detection/resolution during such partial melting curve analysis. In some embodiments in order to maintain a relatively fast cycle, the temperature within a cycle can be controlled to quickly go to the expected temperatures of the melt curve (e.g. partial melt curve) where various amplicons show a signature (e.g. melting temperature as per design of each of the different amplicons) and pass through other temperature points rapidly. Such controlling of the temperature within the cycle can be performed during either a ramping up or a ramping down of the temperature, with better results obtained dependent on the heating method used. FIG. 6B shows a modified cycle of the cycle represented in FIG. 6A whereby the temperature of the cycle corresponding to the transition between the denaturation and the annealing phases is controlled such as to allow for the partial melt curve analysis at the vicinity of the two melting temperature points (TM1) and (TM2). In the embodiment depicted by FIG. 6B, the transition region between the two temperature levels associated to the denaturation and annealing phases is segmented into regions at the vicinity of and including each distinct melting temperature point and segments devoid of a melting point, such as the sum of the segments contain the entire transition region. As depicted by FIG. 6B, segments containing a melting point provide a lower slope corresponding to a lower temperature change of rate such as to allow for better melt curve analysis, whereas segments devoid of a melting point have a larger slope such as to quickly pass through a temperature transition and minimize duration of the cycle. Although in the exemplary case depicted by FIG. 6B the partial melting curve analysis is performed during a ramping down of the temperature profile of the cycle, according to other embodiments of the present disclosure the partial melting curve analysis can be performed during a ramping up of the temperature profile of the cycle as depicted for example in FIGS. 7A and 7B. In some cases, the partial melting curve can be performed only during some (e.g. not all) of the cycles of the amplification process. In a case where the thermal characteristics of the system (e.g. including qPCR fluid) are such that the ramp rate need not be reduced but still a signature is obtained, the cycle can proceed at normal ramp without slowing down near (TM1) or (TM2).

In some embodiments partial melting curve analysis in some of the cycles can be skipped such as to reduce total reaction time (e.g. sum of all cycles times) and then quantify based on threshold only. Normally the $C_T$ value is desired to be quantified. In some embodiments looking for a melt signature (e.g. a specific change in shape/slope of the detected fluorescence versus temperature at a melting temperature point) for an amplicon can be stopped as soon as its signature becomes detectable. In some embodiments it may be desirable to run a final melting curve analysis in order to verify the reaction and cross check against the observed amplicons (e.g. no unexpected amplicons generated).

A partial melting curve analysis algorithm is as follows:

---
Start cycling
    For each cycle
        - If fluorescence is above a threshold (signals start of an
          amplification)
            - Run melting curve for undetected targets
              (or look for expected signature
              instead of going slowly through all temperatures)
            - If a target is detected, mark it and optionally exclude
              analyzing it in next cycles (no need to ramp slowly
              across this melting temperature for next cycles)
            - If all targets are detected, break
    End for
Optionally verify using melting curve at end

---

In some cases it can be desirable to run full melting curve analysis in between cycles of an amplification reaction, at the expense of the extra time required to acquire the melting curve. However, since the melting temperature of each amplicon is known in advance, one can measure fluorescence (e.g. emitted intensity) at particular temperatures (e.g. at the vicinity of a known melting temperature of an amplicon) and skip temperature ranges which do not contain a melting temperature of an amplicon, instead of recording (e.g. measuring fluorescence) at more temperatures as is typically done in a melting curve analysis. By tracking the peaks in observed fluorescence for each of the known melting temperatures (e.g. associated to an amplicon) for each run melting curve, one can detect the presence of an amplicon (e.g. at a concentration). Such a method of accelerating the melting curve analysis can save overall time (e.g. for detection/quantification of amplicons) while quantification can be obtained for many amplicons with different melting temperatures. Also the amplitude information, obtained via the sum amplitude curve, can be used to detect two amplicons with the same or very close melting temperatures. For example, fluorescence increasing at double the rate (e.g. compared to an amplification rate of a single amplicon during an exponential amplification phase) or similar, is indicative of two amplicons being amplified instead of one.

According to a further embodiment of the present disclosure, an algorithm for an accelerated melting curve analysis is presented below. Such algorithm can be used in cases where it is desired to find out the concentration of an amplicon or amplicons (e.g. corresponding $C_T$s) within, for example, a multiplexed reaction. It is assumed that each reaction will go through exponential phase, or in other words that the reactions are proper:

---

Start cycling
    For each cycle
        - Measure fluorescence at temperatures related to each amplicon
        - If a target is detected, mark it and optionally exclude analyzing
          it in next cycles (do not ramp slowly across the melting
          temperature of a detected target for next cycles)
        - If all targets are detected, break
    End for
Optionally verify using melting curve at end

---

Same algorithm presented above can be used in the case of multiple amplicons with similar melting temperatures.

Non-specific probes, such as for example intercalating dyes, can be used to qualitatively find out which amplicon has amplified by using, for example, a melting curve analysis. Non-specific probes can be used to make an assay with targets which need quantification and targets which do not need quantification (e.g. only need to find out their presence and not concentration). Sequence specific probes can be used to measure quantification (e.g. $C_T$ values). In a two channel (e.g. detection) instrument, one channel can be used to perform qualitative analysis of a multiplexed assay using non-specific probes, whereas a second channel can be used to perform a quantification of specific targets of the assay using sequence specific probes. Such a configuration thus provides two degrees of freedom (e.g. color and melting temperature) in multiplex assays.

In the exemplary case of three amplicons, corresponding to a positive control, a negative control and a target, one can use both non-specific dyes and sequence specific hybridization probes (e.g. for all three corresponding amplicons) in a same reaction. According to an embodiment of the present disclosure, such multiplexed reaction can be analyzed, both quantitatively and qualitatively, using two excitation sources and only one detector. For example and as depicted by FIG. 8, if the non-specific dye is SYBR Green and the dye used for sequence specific detection is Alexa Fluor 610 then one can use a blue LED (e.g. 475 nm/25 blue filter) to excite the green dye while the Alexa Fluor is not excited appreciably. This will give melting curve and qualitative answer to the amplification reaction.

Quantification can be determined by measuring the fluorescence during cycles, while a UV LED (e.g. 410 nm/25 UV filter) provides the excitation wavelength, which does not excite the green dye appreciably. The advantage is that only one detector and emission filter is used thus possibly allowing more light capture. In this case the amplification of controls does not interfere with the florescence signal of the target amplicon.

According to further embodiments of the present disclosure, various mathematical transforms and functions used in signal processing (e.g. FFT, DFT, z-transform, etc. . . . ) can be used to compare, match or further analyze signals/amplitudes detected during a multiplexed reaction. Such transforms/functions can detect a phase difference between two shifted waveforms, such as slopes detected and/or assumed, and/or various derivatives of sum amplitude and/or melting curves. They can also help in normalizing the amplitudes and providing more insight into the behavior of the multiplexed reaction than by using only slopes of the observed signals. These transforms/functions can be applied to the entire and/or different parts of the observed/detected signals.

According to a further embodiment of the present disclosure, teachings from the signal processing theory as well as the estimation theory can be used to further analyze the observed/detected signals during a multiplexed amplification reaction. In an exemplary embodiment according to the present disclosure, the estimation model given in FIG. 9 can be used to represent the amplification process.

Figure 9:
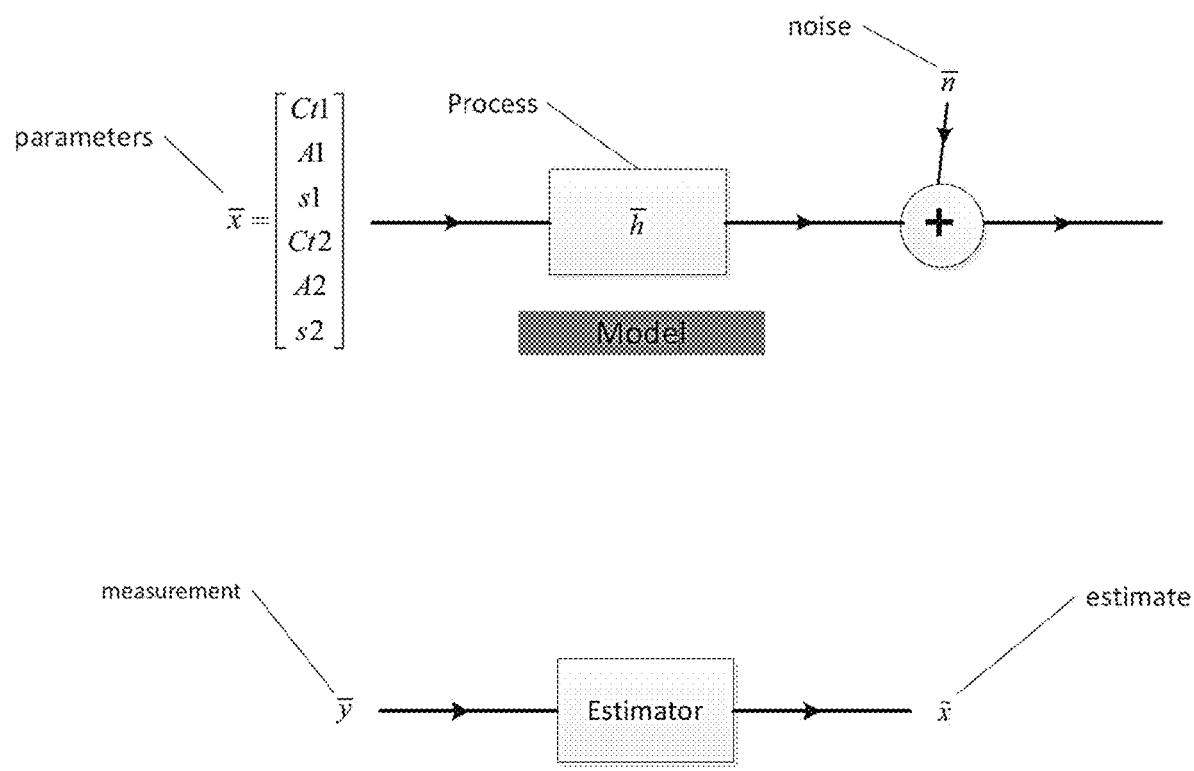
FIG. 9 shows an estimation model which according to an embodiment of the present disclosure can be used to represent a multiplexed amplification process.

In the estimation model depicted by FIG. 9:
    $C_T k = C_T$ of a corresponding amplification
    Ak=amplitude of a corresponding amplification
    Sk=slope/efficiency of a corresponding amplification
    where k=(1, 2, . . . ) depending on the number of multiplexed amplicons.

By feeding an observed signal $\bar{y}$, from the multiplexed amplification reaction, to an estimator corresponding to the modeled process represented by a matrix $\bar{h}$, one can derive an estimation of the process parameter $\bar{x}$, which includes the main information of the reaction (e.g. $C_T$, amplitude, slope/efficiency).

One can use various estimators like ML (maximum likelihood), MAP (Maximum A Priori) and various others to estimate the values of parameters. The process ($\bar{h}$) can be modeled in various ways. It can be modeled recursively and a Kalman filter can be used to smooth out and or estimate the parameters. Various other control algorithms known to a person skilled in the art of signal processing and estimation theory can be used to analyze the observed/detected signals during the multiplexed reaction. As previously mentioned, such algorithms can be implemented in a combination of software/firmware to be used to upgrade an existing instrument and/or used in a new instrument configured to perform the multiplexed reaction (e.g. single channel detector) and/or configured to simply analyze off line data/signals detected/observed.

According to a further embodiment of the present disclosure, quality and concentration of a multiplexed reaction can be obtained by limiting the primers used in the reaction process such as to control the plateau levels of the various amplicons of the multiplexed reaction. Using such method therefore allows to find the $C_T$ value of each amplicon and whether various amplicons amplified using only the amplification curves and without melting curve analysis at the end. By limiting the primers and control the number of cycles it takes to reach plateau phase for various amplicons then an estimate of the slope of fluorescence for each amplicon can be made. In some cases the peaks of derivative and double derivatives would be apart such as to allow easy quantification and detection. In overlapping cases of several $C_T$ values, the prior slope knowledge obtained by limiting the amplicon specific primers can be used to resolve the amplicon amplified. For example, if a slope of the amplification is higher than an expected slope of any of the amplicon (e.g., in case of a same $C_T$ value) then it can be estimated that two amplicons are amplified. Also the fluorescence value at the end of all amplifications can give a sum which can be used to find out how many amplicons did amplify, since plateau level of each amplicon is known per design. Mathematical analysis as described in prior paragraphs can further help to analyze the observed/detected amplitudes/slopes.

Therefore, in accordance with the present disclosure, systems and methods for multiplexing and quantification in PCR with reduced hardware and requirements are provided, which allow detection of different amplicons via a single detector and quantification of said amplicons using known mathematical analysis methods.

The person skilled in the art will be able to extend the teachings of the present disclosure to any type of process which can measure total or targeted amplicon concentration during an amplification, including but not limited to real-time quantitative polymerase chain reaction (qPCR) with fluorescence detection, electrochemical detection or any other real-time detection technique which can quantify the amount of DNA, whether total or specific, in a manner similar to what has already been discussed in the present disclosure. While the devices and methods have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein A number of embodiments of the present inventive concept have been described. Nevertheless, it will be understood that various modifications may be made without departing from the scope of the inventive teachings.

Accordingly, it is to be understood that the inventive concept is not to be limited by the specific illustrated embodiments, but only by the scope of the appended claims. The description may provide examples of similar features as are recited in the claims, but it should not be assumed that such similar features are identical to those in the claims unless such identity is essential to comprehend the scope of the claim. In some instances the intended distinction between claim features and description features is underscored by using slightly different terminology.

The invention claimed is:

1. A method for performing a Polymerase Chain Reaction (PCR) comprising:
   performing a multiplexed PCR in a single channel using a thermal cycler, using a limited set of primers to control plateau levels of a plurality of different amplicons, thereby obtaining different plateau levels for different amplicons, and without performing an end-point melting curve analysis;
   detecting, using a detector, an amplicon of the plurality of different amplicons, the plurality of different amplicons generated during the multiplexed PCR; and
   associating, using a processor controlled analyzer, a cycle threshold (CT) value to an amplicon of the plurality of different amplicons generated during said multiplexed PCR, wherein the associating step comprises:
   (i) receiving a digital representation of a sum amplitude signal, wherein said sum amplitude signal comprises a sum amplitude curve corresponding to a total detected intensity generated by the plurality of different amplicons of said multiplexed PCR, wherein said total detected intensity comprises the signal intensity over a plurality of different wavelengths detected in the single detection channel;
   (ii) measuring an amount of asymmetry in a derivative of said sum amplitude curve;
   (iii) determining a relative position of any two CT values corresponding to any two amplicons from the plurality of different amplicons by using the measured asymmetry; and
   (iv) associating a CT value to an amplicon of said plurality of amplicons, wherein associating the CT value is performed using a characteristic of said sum amplitude signal without determining melting temperatures (Tm) for each of said plurality of different amplicons; and
   wherein the processor controlled analyzer is connected to the thermal cycler for temperature measuring and modulation.

2. The method of claim 1, wherein (ii), (iii), or (iv) is performed using mathematical analysis of the digital representation of the sum amplitude signal, the mathematical analysis being implemented in software and/or firmware code and executed on the processor controlled analyzer.

3. The method of claim 1, wherein the multiplexed PCR further comprises using a plurality of excitation sources.

4. The method of claim 1, wherein the detecting comprises detecting, with a bandwidth filter, a plurality of amplicon signals emitting at different wavelength peaks.

5. The method of claim 1, wherein said characteristic comprises a slope or shape of a portion of said sum amplitude signal.

6. The method of claim 1, wherein a first reporter for a first amplicon and a second reporter for a second amplicon of the plurality of amplicons emit at different wavelength peaks.

7. The method of claim 1, wherein a first reporter for a first amplicon and a second reporter for a second amplicon of the plurality of amplicons emit at a same wavelength peak.

* * * * *